(12) United States Patent
Chatenet et al.

(10) Patent No.: US 12,195,541 B2
(45) Date of Patent: Jan. 14, 2025

(54) GALECTIN-7-SPECIFIC MONOVALENT ANTIBODIES AND USES THEREOF

(71) Applicant: INSTITUT NATIONAL DE LA RECHERCHE SCIENTIFIQUE, Québec (CA)

(72) Inventors: David Chatenet, Lorraine (CA); Nicolas Doucet, Laval (CA); Yves St-Pierre, Laval (CA)

(73) Assignee: Institut National De La Recherche Scientifique, Québec (CA)

( * ) Notice: Subject to any disclaimer, the term of this patent is extended or adjusted under 35 U.S.C. 154(b) by 700 days.

(21) Appl. No.: 17/421,476

(22) PCT Filed: Jan. 9, 2020

(86) PCT No.: PCT/CA2020/050024
§ 371 (c)(1),
(2) Date: Jul. 8, 2021

(87) PCT Pub. No.: WO2020/142847
PCT Pub. Date: Jul. 16, 2020

(65) Prior Publication Data
US 2022/0089746 A1 Mar. 24, 2022

Related U.S. Application Data

(60) Provisional application No. 62/790,197, filed on Jan. 9, 2019.

(51) Int. Cl.
*C07K 16/28* (2006.01)
*G01N 33/533* (2006.01)
*G01N 33/574* (2006.01)

(52) U.S. Cl.
CPC ....... *C07K 16/2851* (2013.01); *G01N 33/533* (2013.01); *G01N 33/57415* (2013.01); *G01N 33/5743* (2013.01); *G01N 33/57449* (2013.01); *G01N 33/57484* (2013.01); *C07K 2317/22* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2020/0115456 A1   4/2020   Liu et al.

FOREIGN PATENT DOCUMENTS

WO   2016187712 A1   12/2016

OTHER PUBLICATIONS

Rabia et al. 2018, Biochem. Eng. J. vol. 137: 365-374.*
Hall, 1992, J. Immunol. vol. 149: 1605-1612.*
Scott, 2012, Nature Reviews, vol. 12: 278-287.*
"International Search Report and Written Opinion corresponding to International Application No. PCT/CA2020/050024 mailed Apr. 14, 2020".
Advedissian, Tamara , et al., "Galectin-7 in Epithelial Homeostasis and Carcinomas", Int. J. Mol. Sci. 18(12):2760-2776 (Dec. 19, 2017).
Dings, Ruud P.M, et al., "Galectins as Molecular Targets for Therapeutic Intervention", Int. J. Mol. Sci. 19(3):905-926 (Mar. 19, 2018).
"Extended European Search Report corresponding to European Application No. 20738736.6 dated Aug. 22, 2022".
Sewgobind, Nishant V, et al., "Functions and Inhibition of Galectin-7, an Emerging Target in Cellular Pathophysiology", Biomolecules 11(11):1720 (Nov. 18, 2021) 25 pages.
Barondes, Samuel H, et al., "Galectins. Structure and function of a large family of animal lectins", J Biol Chem 269(33):20807-20810 (Aug. 19, 1994).
Blanchetot, Christophe , et al., "Neutralizing nanobodies targeting diverse chemokines effectively inhibit chemokine function", J Biol Chem 288(35):25173-25182 (Aug. 30, 2013).
Daley, Donnele , et al., "Dectin-1 activation on macrophages by galectin-9 promotes pancreatic carcinoma and peritumoral immune-tolerance", Nat Med 23(5):556-567 (May 2017).
Degenst, Erwin , et al., "Molecular basis for the preferential cleft recognition by dromedary heavy-chain antibodies", Proc Nat Acad Sci 103(12):4586-4591 (Mar. 21, 2006).
Gauthier, Laurent , et al., "Galectin-1 is a stromal cell ligand of the pre-B cell receptor (BCR) implicated in synapse formation between pre-B and stromal cells and in pre-BCR triggering", Proc Natl Acad Sci 99(20):13014-13019 (Oct. 1, 2002).
Hamers-Casterman, Vrije , et al., "Naturally occurring antibodies devoid of light chains", Nature 363:446-448 (Jun. 3, 1993).
Hu, Yaozhong , et al., "Nanobody-Based Delivery Systems for Diagnosis and Targeted Tumor Therapy", Front Immunol. 8(Article 1442) (Nov. 2, 2017) 17 pages.
Jailkhania, Noor , et al., "Noninvasive imaging of tumor progression, metastasis, and fibrosis using a nanobody targeting the extracellular matrix", PNAS 116(28): 14181-14190 (Jul. 9, 2019).
Kamitori, Shigehiro , "Three-Dimensional Structures of Galectins", Trends Glycosci. Glycotechnol. 30(172):SE41-SE50 (Jan.-May 2018).
Komath, Sneha Sudha, et al., "Beyond carbohydrate binding: new directions in plant lectin research", Org Biomol Chem. 4(6):973-988 (Mar. 21, 2006).

(Continued)

*Primary Examiner* — Amy E Juedes
(74) *Attorney, Agent, or Firm* — Myers Bigel, P.A.

(57) ABSTRACT

Monovalent antibodies such as nanobodies that are specific for galectin-7 are described. These monovalent antibodies are able to interfere with the dimerization of galectin-7, and thus may be used for the treatment of diseases associated with dysregulated galectin-7 expression and/or activity, such as certain types of cancers as well as eye diseases or conditions associated with pathological neovascularization or angiogenesis.

20 Claims, 5 Drawing Sheets
Specification includes a Sequence Listing.

(56) References Cited

OTHER PUBLICATIONS

Leonidas, Demetrios D, et al., "Structural basis for the recognition of carbohydrates by human galectin-7", Biochemistry 37:13930-13940 (Sep. 15, 1988).

Levi, Giovanni, et al., "Prevention and therapy with electrolectin of experimental autoimmune myasthenia gravis in rabbits", Eur J Immunol 13:500-507 (1983).

Liu, Fu-Tong, et al., "Galectins as modulators of tumour progression", Nat Rev Cancer 5:29-41 (Jan. 2005).

Lykken, Jacquelyn M, et al., "Galectin-1 drives lymphome CD20 immunotherapy resistance: validation of a preclinical system to identify resistance mechanisms", Blood 127(15):1886-1895 (Apr. 14, 2016).

Morris, Stephanie, et al., "Quaternary solution structures of galectins-1, -3, and -7", Glycobiology 14(3):293-300 (2004).

Moutel, Sandrine, et al., "NaLi-H1: A universal synthetic library of humanized nanobodies providing highly functional antibodies and intrabodies", Elife 5:e16228 (Jul. 19, 2016) 31 pages.

Nabi, Ivan R, et al., "The galectin lattice at a glance", J Cell Sci 128:2213-2219 (2015).

Offner, Halina, et al., "Recombinant human beta-galactoside binding lectin suppresses clinical and histological signs of experimental autoimmune encephalomyelitis", J Neuroimmunol 28:177-184 (Jan. 1990).

Perillo, Nancy L, et al., "Apoptosis mediated of T cells mediated by galectin-1", Nature 378:736-739 (Dec. 14, 1995).

Rodriguez, Ernesto, et al., "The tumour glyco-code as a novel immune checkpoint for immunotherapy", Nat Rev Immunol 18:204-211 (Mar. 2018).

Salatino, Mariana, et al., "Thwarting galectin-induced immunosuppression in breast cancer", Oncoimmunology 2(5):e24077 (May 2013) 3 pages.

Than, Nándor Gábor, et al., "Placental protein 13 (PP13)—a placental immunoregulatory galectin protecting pregnancy", Front Immunol 5(348):1-25 (Aug. 20, 2014).

Van Woensel, Matthias, et al., "Sensitization of glioblastoma tumor micro-environment to chemo-and immunotherapy by Galectin-1 intranasal knock-down strategy", Sci Rep 7:1217 (Apr. 27, 2017) 14 pages.

Virant, David, et al., "A peptide tag-specific nanobody enables high quality labeling for dSTORM imaging", Nature Communications 9:930 (2018) 14 pages.

Vladoiu, Maria Claudia, et al., "Design of a peptidic inhibitor that targets the dimer interface of a prototypic galectin", Oncotarget 6(38):40970-40980 (Oct. 1, 2015).

Yildirim, Cansu, et al., "Galectin-2 induces a proinflammatory, anti-arteriogenic phenotype in monocytes and macrophages", PLoS One e0124347 (Apr. 17, 2015) 20 pages.

* cited by examiner

```
                    FR1                         CDR1          FR2            CDR2
218_A01    MAEVQLQASGGGFVQPGGSLRLSCAASGAGSRSDVMGWFRQAPGKEREFVSAISGFWGWTT
218_D11    MAEVQLQASGGGFVQPGGSLRLSCAASGDTSRFDVMGWFRQAPGKEREFVSAISWWSSDHI
214_H05    MAEVQLQASGGGFVQPGGSLRLSCAASGTTSNSSGMGWFRQAPGKEREFVSAISWDHGILT
218_F09    MAEVQLQASGGGFVQPGGSLRLSCAASGTTSNGEVMGWFRQAPGKEREFVSAISFGAGSSE
219_F09    MAEVQLQASGGGFVQPGGSLRLSCAASGAYSFESGMGWFRQAPGKEREFVSAISSDADLFS
216_A01    MAEVQLQASGGGFVQPGGSLRLSCAASGRYSRIEIMGWFRQAPGKEREFVSAISSTPSSNE
219_F02    MAEVQLQASGGGFVQPGGSLRLSCAASGSTSYSSTMGWFRQAPGKEREFVSAISFDGTSKP
218_B04    MAEVQLQASGGGFVQPGGSLRLSCAASGRTSSQDIMGWFRQAPGKEREFVSAISDYSGGNV
219_H09    MAEVQLQASGGGFVQPGGSLRLSCAASGSTSYGETMGWFRQAPGKEREFVSAISYYSTRKP
210_A01    MAEVQLQASGGGFVQPGGSLRLSCAASGGGYDWDAMGWFRQAPGKEREFVSAISSNNNGSR
217_C02    MAEVQLQASGGGFVQPGGSLRLSCAASGTYSSIEVMGWFRQAPGKEREFVSAISFEPNEFA
216_D11    MAEVQLQASGGGFVQPGGSLRLSCAASGDTSESTSMGWFRQAPGKEREFVSAISRSSTWDA
Reference  MAEVQLQASGGGFVQPGGSLRLSCAASGXXXXXXXMGWFRQAPGKEREFVSAISXXXXXXX
           ***************************        ******************

FR3                              CDR3
218_A01    YYADSVKGRFTISRDNSKNTVYLQMNSLRAEDTATYYCALGGAPGQTG---------YWGQ
218_D11    YYADSVKGRFTISRDNSKNTVYLQMNSLRAEDTATYYCAYGEYPPRMNR------RPYWGQ
214_H05    YYADSVKGRFTISRDNSKNTVYLQMNSLRAEDTATYYCAHGYVHFNMTHR---HISDYWGQ
218_F09    YYADSVKGRFTISRDNSKNTVYLQMNSLRAEDTATYYCAASWYHSSIG------SMSYWGQ
219_F09    YYADSVKGRFTISRDNSKNTVYLQMNSLRAEDTATYYCAA---FSSGG------ELSYWGQ
216_A01    YYADSVKGRFTISRDNSKNTVYLQMNSLRAEDTATYYCAR---WDWHS------WDTYWGQ
219_F02    YYADSVKGRFTISRDNSKNTVYLQMNSLRAEDTATYYCAAGEWEALMWPPVHDFWIYYWGQ
218_B04    YYADSVKGRFTISRDNSKNTVYLQMNSLRAEDTATYYCAFLGEEKTS---------WYWGQ
219_H09    YYADSVKGRFTISRDNSKNTVYLQMNSLRAEDTATYYCAIVAYIYADGVRGYHQKIDYWGQ
210_A01    YYADSVKGRFTISRDNSKNTVYLQMNSLRAEDTATYYCAAD---------------QYWGQ
217_C02    YYADSVKGRFTISRDNSKNTVYLQMNSLRAEDTATYYCASSVEWRQNGKPNTAS---YWGQ
216_D11    YYADSVKGRFTISRDNSKNTVYLQMNSLRAEDTATYYCAMADIFHPQNASFMK---YWGQ
Reference  YYADSVKGRFTISRDNSKNTVYLQMNSLRAEDTATYYCAXXXXXXXXX---------YWGQ
           **************************************                 ****

FR4
218_A01    GTQVTVSS (SEQ ID NO:1)
218_D11    GTQVTVSS (SEQ ID NO:2)
214_H05    GTQVTVSS (SEQ ID NO:3)
218_F09    GTQVTVSS (SEQ ID NO:4)
219_F09    GTQVTVSS (SEQ ID NO:5)
216_A01    GTQVTVSS (SEQ ID NO:6)
219_F02    GTQVTVSS (SEQ ID NO:7)
218_B04    GTQVTVSS (SEQ ID NO:8)
219_H09    GTQVTVSS (SEQ ID NO:9)
210_A01    GTQVTVSS (SEQ ID NO:10)
217_C02    GTQVTVSS (SEQ ID NO:52)
216_D11    GTQVTVSS (SEQ ID NO:53)
Reference  GTQVTVSS (SEQ ID NO:11)
           ********
```

FIG. 3B

SEQUENCE LISTING

<160> NUMBER OF SEQ ID NOS: 54

<210> SEQ ID NO 1
<211> LENGTH: 121
<212> TYPE: PRT
<213> ORGANISM: Artificial Sequence
<220> FEATURE:
<223> OTHER INFORMATION: Humanized synthetic single domain antibody

<400> SEQUENCE: 1

```
Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Ala Gly Ser Arg
            20                  25                  30

Ser Asp Val Met Gly Trp Phe Arg Gln Ala Pro Gly Lys Glu Arg Glu
        35                  40                  45

Phe Val Ser Ala Ile Ser Gly Phe Trp Gly Trp Thr Thr Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Leu Gly Gly Ala Pro Gly Gln Thr Gly Tyr Trp Gly
            100                 105                 110

Gln Gly Thr Gln Val Thr Val Ser Ser
        115                 120
```

<210> SEQ ID NO 2
<211> LENGTH: 124
<212> TYPE: PRT
<213> ORGANISM: Artificial Sequence
<220> FEATURE:
<223> OTHER INFORMATION: Humanized synthetic single domain antibody

<400> SEQUENCE: 2

```
Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Asp Thr Ser Arg
            20                  25                  30

Phe Asp Val Met Gly Trp Phe Arg Gln Ala Pro Gly Lys Glu Arg Glu
        35                  40                  45

Phe Val Ser Ala Ile Ser Trp Trp Ser Ser Asp His Ile Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Tyr Gly Glu Tyr Pro Pro Arg Met Asn Arg Arg Pro
            100                 105                 110

Tyr Trp Gly Gln Gly Thr Gln Val Thr Val Ser Ser
        115                 120
```

<210> SEQ ID NO 3
<211> LENGTH: 127
<212> TYPE: PRT
<213> ORGANISM: Artificial Sequence
<220> FEATURE:
<223> OTHER INFORMATION: Humanized synthetic single domain antibody

<400> SEQUENCE: 3

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Thr Thr Ser Asn
            20                  25                  30

Ser Ser Gly Met Gly Trp Phe Arg Gln Ala Pro Gly Lys Glu Arg Glu
        35                  40                  45

Phe Val Ser Ala Ile Ser Trp Asp His Gly Ile Leu Thr Tyr Tyr Ala
    50                  55                  60

Asp Ser Val Lys Gly Arg Phe Thr Ile Ser Arg Asp Asn Ser Lys Asn
65              70                  75                  80

Thr Val Tyr Leu Gln Met Asn Ser Leu Arg Ala Glu Asp Thr Ala Thr
                85                  90                  95

Tyr Tyr Cys Ala His Gly Tyr Val His Phe Asn Met Thr His Arg His
            100                 105                 110

Ile Ser Asp Tyr Trp Gly Gln Gly Thr Gln Val Thr Val Ser Ser
            115                 120                 125

<210> SEQ ID NO 4
<211> LENGTH: 124
<212> TYPE: PRT
<213> ORGANISM: Artificial Sequence
<220> FEATURE:
<223> OTHER INFORMATION: Humanized synthetic single domain antibody

<400> SEQUENCE: 4

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Thr Thr Ser Asn
            20                  25                  30

Gly Glu Val Met Gly Trp Phe Arg Gln Ala Pro Gly Lys Glu Arg Glu
        35                  40                  45

Phe Val Ser Ala Ile Ser Phe Gly Ala Gly Ser Ser Glu Tyr Tyr Ala
    50                  55                  60

Asp Ser Val Lys Gly Arg Phe Thr Ile Ser Arg Asp Asn Ser Lys Asn
65              70                  75                  80

Thr Val Tyr Leu Gln Met Asn Ser Leu Arg Ala Glu Asp Thr Ala Thr
                85                  90                  95

Tyr Tyr Cys Ala Ala Ser Trp Tyr His Ser Ser Ile Gly Ser Met Ser
            100                 105                 110

Tyr Trp Gly Gln Gly Thr Gln Val Thr Val Ser Ser
            115                 120

<210> SEQ ID NO 5
<211> LENGTH: 121
<212> TYPE: PRT
<213> ORGANISM: Artificial Sequence
<220> FEATURE:
<223> OTHER INFORMATION: Humanized synthetic single domain antibody

<400> SEQUENCE: 5

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Ala Tyr Ser Phe
            20                  25                  30

Glu Ser Gly Met Gly Trp Phe Arg Gln Ala Pro Gly Lys Glu Arg Glu
        35                  40                  45

Phe Val Ser Ala Ile Ser Ser Asp Ala Asp Leu Phe Ser Tyr Tyr Ala

```
                    50                  55                  60

Asp Ser Val Lys Gly Arg Phe Thr Ile Ser Arg Asp Asn Ser Lys Asn
 65                  70                  75                  80

Thr Val Tyr Leu Gln Met Asn Ser Leu Arg Ala Glu Asp Thr Ala Thr
                     85                  90                  95

Tyr Tyr Cys Ala Ala Phe Ser Ser Gly Glu Leu Ser Tyr Trp Gly
                100                 105                 110

Gln Gly Thr Gln Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Humanized synthetic single domain antibody

<400> SEQUENCE: 6

Met Ala Glu Val Gln Leu Gln Ala Ser Gly Gly Gly Phe Val Gln Pro
 1               5                  10                  15

Gly Gly Ser Leu Arg Leu Ser Cys Ala Ala Ser Gly Arg Tyr Ser Arg
                20                  25                  30

Ile Glu Ile Met Gly Trp Phe Arg Gln Ala Pro Gly Lys Glu Arg Glu
            35                  40                  45

Phe Val Ser Ala Ile Ser Ser Thr Pro Ser Ser Asn Glu Tyr Tyr Ala
         50                  55                  60

Asp Ser Val Lys Gly Arg Phe Thr Ile Ser Arg Asp Asn Ser Lys Asn
 65                  70                  75                  80

Thr Val Tyr Leu Gln Met Asn Ser Leu Arg Ala Glu Asp Thr Ala Thr
                     85                  90                  95

Tyr Tyr Cys Ala Arg Trp Asp Trp His Ser Trp Asp Thr Tyr Trp Gly
                100                 105                 110

Gln Gly Thr Gln Val Thr Val Ser Ser
        115                 120

<210> SEQ ID NO 7
<211> LENGTH: 130
<212> TYPE: PRT
<213> ORGANISM: Artificial Sequence
<220> FEATURE:
<223> OTHER INFORMATION: Humanized synthetic single domain antibody

<400> SEQUENCE: 7

Met Ala Glu Val Gln Leu Gln Ala Ser Gly Gly Gly Phe Val Gln Pro
 1               5                  10                  15

Gly Gly Ser Leu Arg Leu Ser Cys Ala Ala Ser Gly Ser Thr Ser Tyr
                20                  25                  30

Ser Ser Thr Met Gly Trp Phe Arg Gln Ala Pro Gly Lys Glu Arg Glu
            35                  40                  45

Phe Val Ser Ala Ile Ser Phe Asp Gly Thr Ser Lys Pro Tyr Tyr Ala
         50                  55                  60

Asp Ser Val Lys Gly Arg Phe Thr Ile Ser Arg Asp Asn Ser Lys Asn
 65                  70                  75                  80

Thr Val Tyr Leu Gln Met Asn Ser Leu Arg Ala Glu Asp Thr Ala Thr
                     85                  90                  95

Tyr Tyr Cys Ala Ala Gly Glu Trp Glu Ala Leu Met Trp Pro Pro Val
                100                 105                 110
```

His Asp Phe Trp Ile Tyr Tyr Trp Gly Gln Gly Thr Gln Val Thr Val
            115                 120                 125

Ser Ser
    130

<210> SEQ ID NO 8
<211> LENGTH: 121
<212> TYPE: PRT
<213> ORGANISM: Artificial Sequence
<220> FEATURE:
<223> OTHER INFORMATION: Humanized synthetic single domain antibody

<400> SEQUENCE: 8

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Ser Ser
            20                  25                  30

Gln Asp Ile Met Gly Trp Phe Arg Gln Ala Pro Gly Lys Glu Arg Glu
        35                  40                  45

Phe Val Ser Ala Ile Ser Asp Tyr Ser Gly Gly Asn Val Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Phe Leu Gly Glu Gly Lys Thr Ser Trp Tyr Trp Gly
            100                 105                 110

Gln Gly Thr Gln Val Thr Val Ser Ser
            115                 120

<210> SEQ ID NO 9
<211> LENGTH: 130
<212> TYPE: PRT
<213> ORGANISM: Artificial Sequence
<220> FEATURE:
<223> OTHER INFORMATION: Humanized synthetic single domain antibody

<400> SEQUENCE: 9

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Ser Thr Ser Tyr
            20                  25                  30

Gly Glu Thr Met Gly Trp Phe Arg Gln Ala Pro Gly Lys Glu Arg Glu
        35                  40                  45

Phe Val Ser Ala Ile Ser Tyr Tyr Ser Thr Arg Lys Pro Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Ile Val Ala Tyr Ile Tyr Ala Asp Gly Val Arg Gly
            100                 105                 110

Tyr His Gln Lys Ile Asp Tyr Trp Gly Gln Gly Thr Gln Val Thr Val
            115                 120                 125

Ser Ser
    130

<210> SEQ ID NO 10

```
<211> LENGTH: 115
<212> TYPE: PRT
<213> ORGANISM: Artificial Sequence
<220> FEATURE:
<223> OTHER INFORMATION: Humanized synthetic single domain antibody

<400> SEQUENCE: 10

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Gly Gly Tyr Asp
            20                  25                  30

Trp Asp Ala Met Gly Trp Phe Arg Gln Ala Pro Gly Lys Glu Arg Glu
        35                  40                  45

Phe Val Ser Ala Ile Ser Ser Asn Asn Gly Ser Arg Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Ala Asp Gln Tyr Trp Gly Gln Gly Thr Gln Val Thr
            100                 105                 110

Val Ser Ser
        115

<210> SEQ ID NO 11
<211> LENGTH: 121
<212> TYPE: PRT
<213> ORGANISM: Artificial Sequence
<220> FEATURE:
<223> OTHER INFORMATION: Humanized synthetic single domain antibody
<220> FEATURE:
<221> NAME/KEY: VARIANT
<222> LOCATION: (29)..(35)
<223> OTHER INFORMATION: Xaa at each of residues 29 to 35 is any amino
      acid
<220> FEATURE:
<221> NAME/KEY: VARIANT
<222> LOCATION: (55)..(61)
<223> OTHER INFORMATION: Xaa at each of residues 55 to 61 is any amino
      acid
<220> FEATURE:
<221> NAME/KEY: VARIANT
<222> LOCATION: (101)..(109)
<223> OTHER INFORMATION: Xaa at each of residues 101 to 109 is any amino
      acid

<400> SEQUENCE: 11

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Xaa Xaa Xaa Xaa
            20                  25                  30

Xaa Xaa Xaa Met Gly Trp Phe Arg Gln Ala Pro Gly Lys Glu Arg Glu
        35                  40                  45

Phe Val Ser Ala Ile Ser Xaa Xaa Xaa Xaa Xaa Xaa Xaa Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Xaa Xaa Xaa Xaa Xaa Xaa Xaa Xaa Xaa Tyr Trp Gly
            100                 105                 110

Gln Gly Thr Gln Val Thr Val Ser Ser
```

```
                115                 120

<210> SEQ ID NO 12
<211> LENGTH: 7
<212> TYPE: PRT
<213> ORGANISM: Artificial Sequence
<220> FEATURE:
<223> OTHER INFORMATION: CDR1 domain

<400> SEQUENCE: 12

Ala Gly Ser Arg Ser Asp Val
1               5

<210> SEQ ID NO 13
<211> LENGTH: 7
<212> TYPE: PRT
<213> ORGANISM: Artificial Sequence
<220> FEATURE:
<223> OTHER INFORMATION: CDR2 domain

<400> SEQUENCE: 13

Gly Phe Trp Gly Trp Thr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: CDR3 domain

<400> SEQUENCE: 14

Leu Gly Gly Ala Pro Gly Gln Thr Gly
1               5

<210> SEQ ID NO 15
<211> LENGTH: 7
<212> TYPE: PRT
<213> ORGANISM: Artificial Sequence
<220> FEATURE:
<223> OTHER INFORMATION: CDR1 domain

<400> SEQUENCE: 15

Asp Thr Ser Arg Phe Asp Val
1               5

<210> SEQ ID NO 16
<211> LENGTH: 7
<212> TYPE: PRT
<213> ORGANISM: Artificial Sequence
<220> FEATURE:
<223> OTHER INFORMATION: CDR2 domain

<400> SEQUENCE: 16

Trp Trp Ser Ser Asp His Ile
1               5

<210> SEQ ID NO 17
<211> LENGTH: 12
<212> TYPE: PRT
<213> ORGANISM: Artificial Sequence
<220> FEATURE:
<223> OTHER INFORMATION: CDR3 domain

<400> SEQUENCE: 17

Tyr Gly Glu Tyr Pro Pro Arg Met Asn Arg Arg Pro
1               5                   10
```

```
<210> SEQ ID NO 18
<211> LENGTH: 7
<212> TYPE: PRT
<213> ORGANISM: Artificial Sequence
<220> FEATURE:
<223> OTHER INFORMATION: CDR1 domain

<400> SEQUENCE: 18

Thr Thr Ser Asn Ser Ser Gly
1               5

<210> SEQ ID NO 19
<211> LENGTH: 7
<212> TYPE: PRT
<213> ORGANISM: Artificial Sequence
<220> FEATURE:
<223> OTHER INFORMATION: CDR2 domain

<400> SEQUENCE: 19

Trp Asp His Gly Ile Leu Thr
1               5

<210> SEQ ID NO 20
<211> LENGTH: 15
<212> TYPE: PRT
<213> ORGANISM: Artificial Sequence
<220> FEATURE:
<223> OTHER INFORMATION: CDR3 domain

<400> SEQUENCE: 20

His Gly Tyr Val His Phe Asn Met Thr His Arg His Ile Ser Asp
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: CDR1 domain

<400> SEQUENCE: 21

Thr Thr Ser Asn Gly Glu Val
1               5

<210> SEQ ID NO 22
<211> LENGTH: 7
<212> TYPE: PRT
<213> ORGANISM: Artificial Sequence
<220> FEATURE:
<223> OTHER INFORMATION: CDR2 domain

<400> SEQUENCE: 22

Phe Gly Ala Gly Ser Ser Glu
1               5

<210> SEQ ID NO 23
<211> LENGTH: 12
<212> TYPE: PRT
<213> ORGANISM: Artificial Sequence
<220> FEATURE:
<223> OTHER INFORMATION: CDR3 domain

<400> SEQUENCE: 23

Ala Ser Trp Tyr His Ser Ser Ile Gly Ser Met Ser
1               5                   10
```

```
<210> SEQ ID NO 24
<211> LENGTH: 7
<212> TYPE: PRT
<213> ORGANISM: Artificial Sequence
<220> FEATURE:
<223> OTHER INFORMATION: CDR1 domain

<400> SEQUENCE: 24

Ala Tyr Ser Phe Glu Ser Gly
1               5

<210> SEQ ID NO 25
<211> LENGTH: 7
<212> TYPE: PRT
<213> ORGANISM: Artificial Sequence
<220> FEATURE:
<223> OTHER INFORMATION: CDR2 domain

<400> SEQUENCE: 25

Ser Asp Ala Asp Leu Phe Ser
1               5

<210> SEQ ID NO 26
<211> LENGTH: 9
<212> TYPE: PRT
<213> ORGANISM: Artificial Sequence
<220> FEATURE:
<223> OTHER INFORMATION: CDR3 domain

<400> SEQUENCE: 26

Ala Phe Ser Ser Gly Gly Glu Leu Ser
1               5

<210> SEQ ID NO 27
<211> LENGTH: 7
<212> TYPE: PRT
<213> ORGANISM: Artificial Sequence
<220> FEATURE:
<223> OTHER INFORMATION: CDR1 domain

<400> SEQUENCE: 27

Arg Tyr Ser Arg Ile Glu Ile
1               5

<210> SEQ ID NO 28
<211> LENGTH: 7
<212> TYPE: PRT
<213> ORGANISM: Artificial Sequence
<220> FEATURE:
<223> OTHER INFORMATION: CDR2 domain

<400> SEQUENCE: 28

Ser Thr Pro Ser Ser Asn Glu
1               5

<210> SEQ ID NO 29
<211> LENGTH: 9
<212> TYPE: PRT
<213> ORGANISM: Artificial Sequence
<220> FEATURE:
<223> OTHER INFORMATION: CDR3 domain

<400> SEQUENCE: 29

Arg Trp Asp Trp His Ser Trp Asp Thr
1               5
```

```
<210> SEQ ID NO 30
<211> LENGTH: 7
<212> TYPE: PRT
<213> ORGANISM: Artificial Sequence
<220> FEATURE:
<223> OTHER INFORMATION: CDR1 domain

<400> SEQUENCE: 30

Ser Thr Ser Tyr Ser Ser Thr
1               5

<210> SEQ ID NO 31
<211> LENGTH: 7
<212> TYPE: PRT
<213> ORGANISM: Artificial Sequence
<220> FEATURE:
<223> OTHER INFORMATION: CDR2 domain

<400> SEQUENCE: 31

Phe Asp Gly Thr Ser Lys Pro
1               5

<210> SEQ ID NO 32
<211> LENGTH: 18
<212> TYPE: PRT
<213> ORGANISM: Artificial Sequence
<220> FEATURE:
<223> OTHER INFORMATION: CDR3 domain

<400> SEQUENCE: 32

Ala Gly Glu Trp Glu Ala Leu Met Trp Pro Pro Val His Asp Phe Trp
1               5                   10                  15
Ile Tyr

<210> SEQ ID NO 33
<211> LENGTH: 7
<212> TYPE: PRT
<213> ORGANISM: Artificial Sequence
<220> FEATURE:
<223> OTHER INFORMATION: CDR1 domain

<400> SEQUENCE: 33

Arg Thr Ser Ser Gln Asp Ile
1               5

<210> SEQ ID NO 34
<211> LENGTH: 7
<212> TYPE: PRT
<213> ORGANISM: Artificial Sequence
<220> FEATURE:
<223> OTHER INFORMATION: CDR2 domain

<400> SEQUENCE: 34

Asp Tyr Ser Gly Gly Asn Val
1               5

<210> SEQ ID NO 35
<211> LENGTH: 9
<212> TYPE: PRT
<213> ORGANISM: Artificial Sequence
<220> FEATURE:
<223> OTHER INFORMATION: CDR3 DOMAIN

<400> SEQUENCE: 35

Phe Leu Gly Glu Glu Lys Thr Ser Trp
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: CDR1 domain

<400> SEQUENCE: 36

Ser Thr Ser Tyr Gly Glu Thr
1               5

<210> SEQ ID NO 37
<211> LENGTH: 7
<212> TYPE: PRT
<213> ORGANISM: Artificial Sequence
<220> FEATURE:
<223> OTHER INFORMATION: CDR2 domain

<400> SEQUENCE: 37

Tyr Tyr Ser Thr Arg Lys Pro
1               5

<210> SEQ ID NO 38
<211> LENGTH: 18
<212> TYPE: PRT
<213> ORGANISM: Artificial Sequence
<220> FEATURE:
<223> OTHER INFORMATION: CDR3 domain

<400> SEQUENCE: 38

Ile Val Ala Tyr Ile Tyr Ala Asp Gly Val Arg Gly Tyr His Gln Lys
1               5                   10                  15

Ile Asp

<210> SEQ ID NO 39
<211> LENGTH: 7
<212> TYPE: PRT
<213> ORGANISM: Artificial Sequence
<220> FEATURE:
<223> OTHER INFORMATION: CDR1 domain

<400> SEQUENCE: 39

Gly Gly Tyr Asp Trp Asp Ala
1               5

<210> SEQ ID NO 40
<211> LENGTH: 7
<212> TYPE: PRT
<213> ORGANISM: Artificial Sequence
<220> FEATURE:
<223> OTHER INFORMATION: CDR2 domain

<400> SEQUENCE: 40

Ser Asn Asn Asn Gly Ser Arg
1               5

<210> SEQ ID NO 41
<211> LENGTH: 4
<212> TYPE: PRT
<213> ORGANISM: Artificial Sequence
<220> FEATURE:
<223> OTHER INFORMATION: CDR3 DOMAIN
<220> FEATURE:
<221> NAME/KEY: MISC
<222> LOCATION: (4)..(4)
<223> OTHER INFORMATION: X at position 4 is absent
```

```
<400> SEQUENCE: 41

Ala Asp Gln Xaa
1

<210> SEQ ID NO 42
<211> LENGTH: 7
<212> TYPE: PRT
<213> ORGANISM: Artificial Sequence
<220> FEATURE:
<223> OTHER INFORMATION: CDR1 domain

<400> SEQUENCE: 42

Thr Tyr Ser Ser Ile Glu Val
1               5

<210> SEQ ID NO 43
<211> LENGTH: 7
<212> TYPE: PRT
<213> ORGANISM: Artificial Sequence
<220> FEATURE:
<223> OTHER INFORMATION: CDR2 domain

<400> SEQUENCE: 43

Phe Glu Pro Asn Glu Phe Ala
1               5

<210> SEQ ID NO 44
<211> LENGTH: 15
<212> TYPE: PRT
<213> ORGANISM: Artificial Sequence
<220> FEATURE:
<223> OTHER INFORMATION: CDR3 domain

<400> SEQUENCE: 44

Ser Ser Val Glu Trp Arg Gln Asn Gly Lys Pro Asn Thr Ala Ser
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: CDR1 domain

<400> SEQUENCE: 45

Asp Thr Ser Glu Ser Thr Ser
1               5

<210> SEQ ID NO 46
<211> LENGTH: 7
<212> TYPE: PRT
<213> ORGANISM: Artificial Sequence
<220> FEATURE:
<223> OTHER INFORMATION: CDR2 domain

<400> SEQUENCE: 46

Arg Ser Ser Thr Trp Asp Ala
1               5

<210> SEQ ID NO 47
<211> LENGTH: 15
<212> TYPE: PRT
<213> ORGANISM: Artificial Sequence
<220> FEATURE:
<223> OTHER INFORMATION: CDR3 domain

<400> SEQUENCE: 47
```

Met Ala Asp Ile Phe Asp His Pro Gln Asn Ala Ser Phe Met Lys
1               5                   10                  15

<210> SEQ ID NO 48
<211> LENGTH: 28
<212> TYPE: PRT
<213> ORGANISM: Artificial Sequence
<220> FEATURE:
<223> OTHER INFORMATION: FR1 domain

<400> SEQUENCE: 48

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly
            20                  25

<210> SEQ ID NO 49
<211> LENGTH: 19
<212> TYPE: PRT
<213> ORGANISM: Artificial Sequence
<220> FEATURE:
<223> OTHER INFORMATION: FR2 domain

<400> SEQUENCE: 49

Met Gly Trp Phe Arg Gln Ala Pro Gly Lys Glu Arg Glu Phe Val Ser
1               5                   10                  15

Ala Ile Ser

<210> SEQ ID NO 50
<211> LENGTH: 39
<212> TYPE: PRT
<213> ORGANISM: Artificial Sequence
<220> FEATURE:
<223> OTHER INFORMATION: FR3 domain

<400> SEQUENCE: 50

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 51
<211> LENGTH: 12
<212> TYPE: PRT
<213> ORGANISM: Artificial Sequence
<220> FEATURE:
<223> OTHER INFORMATION: FR4 domain

<400> SEQUENCE: 51

Tyr Trp Gly Gln Gly Thr Gln Val Thr Val Ser Ser
1               5                   10

<210> SEQ ID NO 52
<211> LENGTH: 127
<212> TYPE: PRT
<213> ORGANISM: Artificial Sequence
<220> FEATURE:
<223> OTHER INFORMATION: Recombinant antibody

<400> SEQUENCE: 52

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Thr Tyr Ser Ser
            20                  25                  30

Ile Glu Val Met Gly Trp Phe Arg Gln Ala Pro Gly Lys Glu Arg Glu
            35                  40                  45

Phe Val Ser Ala Ile Ser Phe Glu Pro Asn Glu Phe Ala Tyr Tyr Ala
50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
            85                  90                  95

Tyr Tyr Cys Ala Ser Ser Val Glu Trp Arg Gln Asn Gly Lys Pro Asn
            100                 105                 110

Thr Ala Ser Tyr Trp Gly Gln Gly Thr Gln Val Thr Val Ser Ser
            115                 120                 125

<210> SEQ ID NO 53
<211> LENGTH: 127
<212> TYPE: PRT
<213> ORGANISM: Artificial Sequence
<220> FEATURE:
<223> OTHER INFORMATION: Recombinant antibody

<400> SEQUENCE: 53

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Asp Thr Ser Glu
            20                  25                  30

Ser Thr Ser Met Gly Trp Phe Arg Gln Ala Pro Gly Lys Glu Arg Glu
            35                  40                  45

Phe Val Ser Ala Ile Ser Arg Ser Ser Thr Trp Asp Ala Tyr Tyr Ala
50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
            85                  90                  95

Tyr Tyr Cys Ala Met Ala Asp Ile Phe Asp His Pro Gln Asn Ala Ser
            100                 105                 110

Phe Met Lys Tyr Trp Gly Gln Gly Thr Gln Val Thr Val Ser Ser
            115                 120                 125

<210> SEQ ID NO 54
<211> LENGTH: 54
<212> TYPE: PRT
<213> ORGANISM: Artificial Sequence
<220> FEATURE:
<223> OTHER INFORMATION: Synthetic tag

<400> SEQUENCE: 54

Ala Ala Ala His His His His His His Gly Ala Ala Glu Gln Lys Leu
1               5                   10                  15

Ile Ser Glu Glu Asp Leu Asn Gly Ala Ala Glu Gln Lys Leu Ile Ser
            20                  25                  30

Glu Glu Asp Leu Asn Gly Ala Ala Glu Gln Lys Leu Ile Ser Glu Glu
            35                  40                  45

Asp Leu Asn Gly Ala Ala
50

GALECTIN-7-SPECIFIC MONOVALENT ANTIBODIES AND USES THEREOF

CROSS REFERENCE TO RELATED APPLICATIONS

The present application is a National Entry Application of PCT application No. PCT/CA2020/050024, filed on Jan. 9, 2020, which claims benefit of U.S. provisional application No. 62/790,197 filed on Jan. 9, 2019. All documents above are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9355.12_ST25.txt, 24,677 bytes in size, generated on Jul. 6, 2021 and filed via EFS-Web, is provided in lieu of a paper copy. This Sequence Listing is hereby incorporated by reference into the specification for its disclosures.

TECHNICAL FIELD

The present disclosure generally relates to galectins, and more specifically to the modulation of galectin-7 activity.

BACKGROUND ART

Galectins (GAL) are multifunctional proteins that belong to the animal lectin family. All galectins share similar binding affinities to β-galactosides and display high amino acid sequence homology among their carbohydrate-recognition domains (CRDs) [Barondes et al., 1994]. In mammals, 19 different members of this family have been identified, with 13 of them being expressed in humans (GAL-5, -6, -11, -15, -16, -19, and -20 are not found in humans) (FIG. 1). Galectins are divided into three sub-groups according to their structure: prototypic galectins containing one CRD (GAL-1, -2, -5, -7, -10, -11, -13, -14, -15, -16, -17, -19, and -20), tandem-repeat galectins containing two covalently linked CRDs (GAL-4, -6, -8, -9 and -12) and chimera-type galectins containing multiple CRDs linked by their amino-terminal domain (GAL-3). While these proteins perform homeostatic functions inside normal cells, under pathological or stress conditions, galectins are released either passively from dead cells or actively via non-classical secretion pathways. Once released into the extracellular milieu, they bind to repeating units of high density N- and O-glycans on the peptide backbone of membrane receptors via their CRD [Nabi et al., 2015]. This ability of galectins to promote the packing of glycosylated receptors into an ordered cross-linked lattice at the cell surface is facilitated by their inherent multivalency. Such multivalency is a common feature of lactose- and galactose-binding lectins and is the results of a selective pressure for stabilizing a multivalent quaternary structure to increase ligand affinity. This occurs either following the association of different monomers (in the case of prototypic galectins) or via multiple CRDs encoded within a single polypeptide chain (for tandem-repeat). The importance of oligomerization has been particularly well studied in the case of GAL-3, which forms oligomers via its N-terminal peptide when bound to cell surface glycoreceptors.

Normally, galectins contribute to the generation of an immune-privileged environment at the maternal-fetal interface [Than et al., 2014]. Their immunosuppressive role is well illustrated by older studies showing that administration of recombinant prototypic GAL-1 prevents progression of autoimmune disorders [Levi et al., 1983; Offner et al., 1990]. Such an immunosuppressive role is at least in part due to the ability of galectins to kill cancer-killing immune cells. This was first reported more than 20 years ago in a landmark paper published in Nature by the group of Linda Baum [Perillo et al., 1995]. This immunosuppressive activity of galectins is now recognized as a significant obstacle to successful cancer immunotherapy [Liu and Rabinovich, 2005; Salatino et al., 2013; Rodriguez et al., 2018]. This has been well established in several types of cancers. In lymphoma, for example, secretion of GAL-1 is responsible for resistance to anti-CD20 immunotherapy [Lykken et al., 2016]. Targeting GAL-9 has also been shown to be a valuable alternative to improve immunotherapy against pancreatic ductal adenocarcinoma [Daley et al., 2017]. Neutralization of galectins by intranasal delivery of GAL-1-specific siRNA also increases the efficiency of immune-checkpoint inhibitors for the treatment of glioblastoma [Van Woensel et al., 2017]. The immunosuppressive role of galectins in cancer has attracted the interest of many researchers involved in the development of novel immunotherapies that target immune checkpoints, a valuable strategy for the treatment of aggressive types of cancer, especially for those harboring an immune phenotype.

Despite the growing literature on the importance of galectins in cancer, clinical testing of galectin inhibitors for the treatment of cancer has, until now, fell short of expectations and generated some skepticism with regards to their potential for the treatment of cancer. This is largely due to the lack of highly specific, high affinity galectin inhibitors and our limited understanding of their role at different steps of cancer progression. In most cases, these inhibitors are high molecular weight, naturally occurring polysaccharides that are used to block the glycan-binding site of galectins, thereby inhibiting the binding of extracellular galectins to glycosylated receptors/proteins. Development of specific inhibitors for galectins, however, is challenging given their high degree of structural homology in their glycan binding site (GBS). Another obstacle to the development of galectin-specific inhibitors is the fact that very little is currently known about the three-dimensional features of less-well known galectins, such as GAL-14. So far, most of the inhibitors that have been developed until now are targeting the GBS and exclusively focus on GAL-1 and GAL-3. Moreover, there is recent evidence that some galectins do not always accomplish their function via their GBS. This should come as no surprise because we have known for a long time that lectin can bind non-carbohydrate ligands, often exhibiting higher affinities than their 'natural' saccharide ligands [reviewed by Komath et al., 2006]. This is particularly well illustrated during the formation of an immune synapse following the binding of GAL-1 to the non-glycosylated surrogate light chain of the pre-B cell receptor expressed on the surface of immature B cells [Gauthier et al., 2002]. GAL-2 also binds to cell surface receptors on human monocytes [Yildirim et al., 2015]. These CRD-independent functions represent a paradigm shift in our understanding of galectin function and the development of galectin-specific antagonists. Consequently, there is a need to refine the strategies for the development of new, effective, and specific galectin tools.

The validation of Galectin-7 (GAL-7) as a target for therapeutic purposes in cancer has been well established in multiple pre-clinical animal models, most notably in aggressive subtypes of breast cancers, such as triple-negative breast cancer. These cancer cells express abnormally high levels of GAL-7 which is locally released in the extracellular milieu. Extracellular GAL-7 will promote cancer by at least two different mechanisms. First, through an autocrine mechanism, they bind to cell surface receptors of cancer cells and induce de novo transcriptional activation of Igals7, which in turn render cells resistant to pro-apoptotic drugs. Secondly, the binding of extracellular GAL-7 to glycoreceptors expressed in infiltrated immune cells triggers a cascade of signaling events that either leads to apoptosis of cancer-killing T cells or alters their regulatory functions, helping tumors evade anti-tumor immunity. The immunosuppressive activity of GAL-7 is thus a major obstacle to successful cancer immunotherapy. Given the pro-tumorigenic activity of GAL-7, considerable efforts have been directed towards the development of carbohydrate-based inhibitors that would limit the binding of GAL-7 to glycosylated residues on cell surface receptors. The major problem is that despite decades of research, the progression in this field has been relatively slow. There is yet no specific GAL-7 inhibitor on the market.

There is thus a need for agents and methods for targeting GAL-7 and/or modulating GAL-7 activity.

The present description refers to a number of documents, the content of which is herein incorporated by reference in their entirety.

SUMMARY

The present disclosure provides the following items 1 to 79:

1. A monovalent antibody that specifically binds to human galectin-7 (hGAL-7) dimerization, wherein the monovalent antibody comprises one of the following combinations of complementarity determining regions (CDRs):
   (a) a CDR1 comprising an amino acid sequence having at least 80% identity with the sequence AGSRSDV (SEQ ID NO:12); a CDR2 comprising an amino acid sequence having at least 80% identity with the sequence GFWGWTT (SEQ ID NO:13); and a CDR3 comprising an amino acid sequence having at least 80% identity with the sequence LGGAPGQTG (SEQ ID NO:14);
   (b) a CDR1 comprising an amino acid sequence having at least 80% identity with the sequence DTSRFDV (SEQ ID NO:15); a CDR2 comprising an amino acid sequence having at least 80% identity with the sequence WWSSDHI (SEQ ID NO:16); and a CDR3 comprising an amino acid sequence having at least 80% identity with the sequence YGEYPPRMNRRP (SEQ ID NO:17);
   (c) a CDR1 comprising an amino acid sequence having at least 80% identity with the sequence TTSNSSG (SEQ ID NO:18); a CDR2 comprising an amino acid sequence having at least 80% identity with the sequence WDHGILT (SEQ ID NO:19); and a CDR3 comprising an amino acid sequence having at least 80% identity with the sequence HGYVHFNMTHRHISD (SEQ ID NO:20);
   (d) a CDR1 comprising an amino acid sequence having at least 80% identity with the sequence TTSNGEV (SEQ ID NO:21); a CDR2 comprising an amino acid sequence having at least 80% identity with the sequence FGAGSSE (SEQ ID NO:22); and a CDR3 comprising an amino acid sequence having at least 80% identity with the sequence ASWYHSSIGSMS (SEQ ID NO:23);
   (e) a CDR1 comprising or consisting of an amino acid sequence having at least 80% identity with the sequence AYSFESG (SEQ ID NO:24); a CDR2 comprising an amino acid sequence having at least 80% identity with the sequence SDADLFS (SEQ ID NO:25); and a CDR3 comprising an amino acid sequence having at least 80% identity with the sequence AFSSGGELS (SEQ ID NO:26);
   (f) a CDR1 comprising an amino acid sequence having at least 80% identity with the sequence RYSRIEI (SEQ ID NO:27); a CDR2 comprising an amino acid sequence having at least 80% identity with the sequence STPSSNE (SEQ ID NO:28); and a CDR3 comprising an amino acid sequence having at least 80% identity with the sequence RWDWHSWDT (SEQ ID NO:29);
   (g) a CDR1 comprising an amino acid sequence having at least 80% identity with the sequence STSYSST (SEQ ID NO:30); a CDR2 comprising an amino acid sequence having at least 80% identity with the sequence FDGTSKP (SEQ ID NO:31); and a CDR3 comprising an amino acid sequence having at least 80% identity with the sequence AGEWEALMWPPVHDFWIY (SEQ ID NO:32);
   (h) a CDR1 comprising an amino acid sequence having at least 80% identity with the sequence RTSSQDI (SEQ ID NO:33); a CDR2 comprising an amino acid sequence having at least 80% identity with the sequence DYSGGNV (SEQ ID NO:34); and a CDR3 comprising an amino acid sequence having at least 80% identity with the sequence FLGEEKTSW (SEQ ID NO:35);
   (i) a CDR1 comprising an amino acid sequence having at least 80% identity with the sequence STSYGET (SEQ ID NO:36); a CDR2 comprising an amino acid sequence having at least 80% identity with the sequence YYSTRKP (SEQ ID NO:37); and a CDR3 comprising an amino acid sequence having at least 80% identity with the sequence IVAYIYADGVRGYHQKID (SEQ ID NO:38);
   (j) a CDR1 comprising an amino acid sequence having at least 80% identity with the sequence GGYDWDA (SEQ ID NO:39); a CDR2 comprising an amino acid sequence having at least 80% identity with the sequence SNNNGSR (SEQ ID NO:40); and a CDR3 comprising an amino acid sequence having at least 80% identity with the sequence ADQ (SEQ ID NO:41);
   (k) a CDR1 comprising an amino acid sequence having at least 80% identity with the sequence TYSSIEV (SEQ ID NO:42); a CDR2 comprising an amino acid sequence having at least 80% identity with the sequence FEPNEFA (SEQ ID NO:43); and a CDR3 comprising an amino acid sequence having at least 80% identity with the sequence SSVEWRQNGKPNTAS (SEQ ID NO:44);
   (l) a CDR1 comprising an amino acid sequence having at least 80% identity with the sequence DTSESTS (SEQ ID NO:45); a CDR2 comprising an amino acid sequence having at least 80% identity with the sequence RSSTWDA (SEQ ID NO:46); and a CDR3 comprising an amino acid sequence having at least 80% identity with the sequence MADIFDHPQNASFMK (SEQ ID NO:47);

2. The monovalent antibody of item 1, which comprises one of the following combinations of CDRs:
   (a) a CDR1 comprising an amino acid sequence having at least 90% identity with the sequence AGSRSDV (SEQ ID NO:12); a CDR2 comprising an amino acid sequence having at least 90% identity with the sequence GFWGWTT (SEQ ID NO:13); and a CDR3 comprising an amino acid sequence having at least 90% identity with the sequence LGGAPGQTG (SEQ ID NO:14);

(b) a CDR1 comprising an amino acid sequence having at least 90% identity with the sequence DTSRFDV (SEQ ID NO:15); a CDR2 comprising an amino acid sequence having at least 90% identity with the sequence WWSSDHI (SEQ ID NO:16); and a CDR3 comprising an amino acid sequence having at least 90% identity with the sequence YGEYPPRMNRRP (SEQ ID NO:17);

(c) a CDR1 comprising an amino acid sequence having at least 90% identity with the sequence TTSNSSG (SEQ ID NO:18); a CDR2 comprising an amino acid sequence having at least 90% identity with the sequence WDHGILT (SEQ ID NO:19); and a CDR3 comprising an amino acid sequence having at least 90% identity with the sequence HGYVHFNMTHRHISD (SEQ ID NO:20);

(d) a CDR1 comprising an amino acid sequence having at least 90% identity with the sequence TTSNGEV (SEQ ID NO:21); a CDR2 comprising an amino acid sequence having at least 90% identity with the sequence FGAGSSE (SEQ ID NO:22); and a CDR3 comprising an amino acid sequence having at least 90% identity with the sequence ASWYHSSIGSMS (SEQ ID NO:23);

(e) a CDR1 comprising or consisting of an amino acid sequence having at least 90% identity with the sequence AYSFESG (SEQ ID NO:24); a CDR2 comprising an amino acid sequence having at least 90% identity with the sequence SDADLFS (SEQ ID NO:25); and a CDR3 comprising an amino acid sequence having at least 90% identity with the sequence AFSSGGELS (SEQ ID NO:26);

(f) a CDR1 comprising an amino acid sequence having at least 90% identity with the sequence RYSRIEI (SEQ ID NO:27); a CDR2 comprising an amino acid sequence having at least 90% identity with the sequence STPSSNE (SEQ ID NO:28); and a CDR3 comprising an amino acid sequence having at least 90% identity with the sequence RWDWHSWDT (SEQ ID NO:29);

(g) a CDR1 comprising an amino acid sequence having at least 90% identity with the sequence STSYSST (SEQ ID NO:30); a CDR2 comprising an amino acid sequence having at least 90% identity with the sequence FDGTSKP (SEQ ID NO:31); and a CDR3 comprising an amino acid sequence having at least 90% identity with the sequence AGEWEALMWPPVHDFWIY (SEQ ID NO:32);

(h) a CDR1 comprising an amino acid sequence having at least 90% identity with the sequence RTSSQDI (SEQ ID NO:33); a CDR2 comprising an amino acid sequence having at least 90% identity with the sequence DYSGGNV (SEQ ID NO:34); and a CDR3 comprising an amino acid sequence having at least 90% identity with the sequence FLGEEKTSW (SEQ ID NO:35);

(i) a CDR1 comprising an amino acid sequence having at least 90% identity with the sequence STSYGET (SEQ ID NO:36); a CDR2 comprising an amino acid sequence having at least 90% identity with the sequence YYSTRKP (SEQ ID NO:37); and a CDR3 comprising an amino acid sequence having at least 90% identity with the sequence IVAYIYADGVRGYHQKID (SEQ ID NO:38);

(j) a CDR1 comprising an amino acid sequence having at least 90% identity with the sequence GGYDWDA (SEQ ID NO:39); a CDR2 comprising an amino acid sequence having at least 90% identity with the sequence SNNNGSR (SEQ ID NO:40); and a CDR3 comprising an amino acid sequence having at least 90% identity with the sequence ADQ (SEQ ID NO:41);

(k) a CDR1 comprising an amino acid sequence having at least 90% identity with the sequence TYSSIEV (SEQ ID NO:42); a CDR2 comprising an amino acid sequence having at least 90% identity with the sequence FEPNEFA (SEQ ID NO:43); and a CDR3 comprising an amino acid sequence having at least 90% identity with the sequence SSVEWRQNGKPNTAS (SEQ ID NO:44); or (l) a CDR1 comprising an amino acid sequence having at least 90% identity with the sequence DTSESTS (SEQ ID NO:45); a CDR2 comprising an amino acid sequence having at least 90% identity with the sequence RSSTWDA (SEQ ID NO:46); and a CDR3 comprising an amino acid sequence having at least 90% identity with the sequence MADIFDHPQNASFMK (SEQ ID NO:47).

3. The monovalent antibody of item 2, which comprises one of the following combinations of CDRs:

(a) a CDR1 comprising the sequence AGSRSDV (SEQ ID NO:12); a CDR2 comprising the sequence GFWGWTT (SEQ ID NO:13); and a CDR3 comprising the sequence LGGAPGQTG (SEQ ID NO:14);

(b) a CDR1 comprising the sequence DTSRFDV (SEQ ID NO:15); a CDR2 comprising the sequence WWSSDHI (SEQ ID NO:16); and a CDR3 comprising the sequence YGEYPPRMNRRP (SEQ ID NO:17);

(c) a CDR1 comprising the sequence TTSNSSG (SEQ ID NO:18); a CDR2 comprising the sequence WDHGILT (SEQ ID NO:19); and a CDR3 comprising the sequence HGYVHFNMTHRHISD (SEQ ID NO:20);

(d) a CDR1 comprising the sequence TTSNGEV (SEQ ID NO:21); a CDR2 comprising the sequence FGAGSSE (SEQ ID NO:22); and a CDR3 comprising the sequence ASWYHSSIGSMS (SEQ ID NO:23);

(e) a CDR1 comprising or consisting of an amino acid sequence having at least 90% identity with the sequence AYSFESG (SEQ ID NO:24); a CDR2 comprising the sequence SDADLFS (SEQ ID NO:25); and a CDR3 comprising the sequence AFSSGGELS (SEQ ID NO:26);

(f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29);

(g) a CDR1 comprising the sequence STSYSST (SEQ ID NO:30); a CDR2 comprising the sequence FDGTSKP (SEQ ID NO:31); and a CDR3 comprising the sequence AGEWEALMWPPVHDFWIY (SEQ ID NO:32);

(h) a CDR1 comprising the sequence RTSSQDI (SEQ ID NO:33); a CDR2 comprising the sequence DYSGGNV (SEQ ID NO:34); and a CDR3 comprising the sequence FLGEEKTSW (SEQ ID NO:35);

(i) a CDR1 comprising the sequence STSYGET (SEQ ID NO:36); a CDR2 comprising the sequence YYSTRKP (SEQ ID NO:37); and a CDR3 comprising the sequence IVAYIYADGVRGYHQKID (SEQ ID NO:38);
(j) a CDR1 comprising the sequence GGYDWDA (SEQ ID NO:39); a CDR2 comprising the sequence SNNNGSR (SEQ ID NO:40); and a CDR3 comprising the sequence ADQ (SEQ ID NO:41);
(k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44); or
(l) a CDR1 comprising the sequence DTSESTS (SEQ ID NO:45); a CDR2 comprising the sequence RSSTWDA (SEQ ID NO:46); and a CDR3 comprising the sequence MADIFDHPQNASFMK (SEQ ID NO:47).

4. The monovalent antibody of item 1, wherein the monovalent antibody inhibits hGAL-7 activity and comprises one of the following combinations of CDRs:
(f) a CDR1 comprising an amino acid sequence having at least 80% identity with the sequence RYSRIEI (SEQ ID NO:27); a CDR2 comprising an amino acid sequence having at least 80% identity with the sequence STPSSNE (SEQ ID NO:28); and a CDR3 comprising an amino acid sequence having at least 80% identity with the sequence RWDWHSWDT (SEQ ID NO:29);
(g) a CDR1 comprising an amino acid sequence having at least 80% identity with the sequence STSYSST (SEQ ID NO:30); a CDR2 comprising an amino acid sequence having at least 80% identity with the sequence FDGTSKP (SEQ ID NO:31); and a CDR3 comprising an amino acid sequence having at least 80% identity with the sequence AGEWEALMWPPVHDFWIY (SEQ ID NO:32);
(i) a CDR1 comprising an amino acid sequence having at least 80% identity with the sequence STSYGET (SEQ ID NO:36); a CDR2 comprising an amino acid sequence having at least 80% identity with the sequence YYSTRKP (SEQ ID NO:37); and a CDR3 comprising an amino acid sequence having at least 80% identity with the sequence IVAYIYADGVRGYHQKID (SEQ ID NO:38); or
(k) a CDR1 comprising an amino acid sequence having at least 80% identity with the sequence TYSSIEV (SEQ ID NO:42); a CDR2 comprising an amino acid sequence having at least 80% identity with the sequence FEPNEFA (SEQ ID NO:43); and a CDR3 comprising an amino acid sequence having at least 80% identity with the sequence SSVEWRQNGKPNTAS (SEQ ID NO:44).

5. The monovalent antibody of item 1, wherein the monovalent antibody inhibits hGAL-7 dimerization and comprises one of the following combinations of CDRs:
(f) a CDR1 comprising an amino acid sequence having at least 80% identity with the sequence RYSRIEI (SEQ ID NO:27); a CDR2 comprising an amino acid sequence having at least 80% identity with the sequence STPSSNE (SEQ ID NO:28); and a CDR3 comprising an amino acid sequence having at least 80% identity with the sequence RWDWHSWDT (SEQ ID NO:29); or
(k) a CDR1 comprising an amino acid sequence having at least 80% identity with the sequence TYSSIEV (SEQ ID NO:42); a CDR2 comprising an amino acid sequence having at least 80% identity with the sequence FEPNEFA (SEQ ID NO:43); and a CDR3 comprising an amino acid sequence having at least 80% identity with the sequence SSVEWRQNGKPNTAS (SEQ ID NO:44).

6. The monovalent antibody of item 4, wherein the monovalent antibody comprises one of the following combinations of CDRs:
(f) a CDR1 comprising an amino acid sequence having at least 90% identity with the sequence RYSRIEI (SEQ ID NO:27); a CDR2 comprising an amino acid sequence having at least 90% identity with the sequence STPSSNE (SEQ ID NO:28); and a CDR3 comprising an amino acid sequence having at least 90% identity with the sequence RWDWHSWDT (SEQ ID NO:29);
(g) a CDR1 comprising an amino acid sequence having at least 90% identity with the sequence STSYSST (SEQ ID NO:30); a CDR2 comprising an amino acid sequence having at least 90% identity with the sequence FDGTSKP (SEQ ID NO:31); and a CDR3 comprising an amino acid sequence having at least 90% identity with the sequence AGEWEALMWPPVHDFWIY (SEQ ID NO:32);
(i) a CDR1 comprising an amino acid sequence having at least 90% identity with the sequence STSYGET (SEQ ID NO:36); a CDR2 comprising an amino acid sequence having at least 90% identity with the sequence YYSTRKP (SEQ ID NO:37); and a CDR3 comprising an amino acid sequence having at least 90% identity with the sequence IVAYIYADGVRGYHQKID (SEQ ID NO:38); or
(k) a CDR1 comprising an amino acid sequence having at least 90% identity with the sequence TYSSIEV (SEQ ID NO:42); a CDR2 comprising an amino acid sequence having at least 90% identity with the sequence FEPNEFA (SEQ ID NO:43); and a CDR3 comprising an amino acid sequence having at least 90% identity with the sequence SSVEWRQNGKPNTAS (SEQ ID NO:44).

7. The monovalent antibody of item 6, wherein the monovalent antibody comprises one of the following combinations of CDRs:
(f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29);
(g) a CDR1 comprising the sequence STSYSST (SEQ ID NO:30); a CDR2 comprising the sequence FDGTSKP (SEQ ID NO:31); and a CDR3 comprising the sequence AGEWEALMWPPVHDFWIY (SEQ ID NO:32);
(i) a CDR1 comprising the sequence STSYGET (SEQ ID NO:36); a CDR2 comprising the sequence YYSTRKP (SEQ ID NO:37); and a CDR3 comprising the sequence IVAYIYADGVRGYHQKID (SEQ ID NO:38); or
(k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44).

8. The monovalent antibody of item 5, wherein the monovalent antibody comprises one of the following combinations of CDRs:
(f) a CDR1 comprising an amino acid sequence having at least 90% identity with the sequence RYSRIEI (SEQ ID NO:27); a CDR2 comprising an amino acid sequence having at least 90% identity with the sequence STPSSNE (SEQ ID NO:28); and a CDR3 comprising an amino acid sequence having at least 90% identity with the sequence RWDWHSWDT (SEQ ID NO:29); or (k) a CDR1 comprising an amino acid sequence having at least 90% identity with the sequence TYSSIEV (SEQ ID NO:42); a CDR2 comprising an amino acid sequence having at least 90% identity with the sequence FEPNEFA (SEQ ID NO:43); and a CDR3 comprising an amino acid sequence having at least 90% identity with the sequence SSVEWRQNGKPNTAS (SEQ ID NO:44).

9. The monovalent antibody of item 8, wherein the monovalent antibody comprises one of the following combinations of CDRs:

(f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29); or (k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44).

10. The monovalent antibody of any one of items 1 to 9, wherein the monovalent antibody is a single-domain antibody.

11. The monovalent antibody of any one of items 1 to 10, which comprises:

(i) a framework region (FR) 1 comprising an amino acid sequence having at least 50% identity with the sequence MAEVQLQASGGGFVQPGGSLRLSCAASG (SEQ ID NO:48);

(ii) a FR2 comprising an amino acid sequence having at least 50% identity with the sequence MGWFRQAPGKEREFVSAIS (SEQ ID NO:49);

(iii) a FR3 comprising or consisting of an amino acid sequence having at least 50% identity with the sequence YYADSVKGRFTISRDNSKNTVYLQMNSLRAEDTATYYCA (SEQ ID NO:50);

(iv) a FR4 comprising an amino acid sequence having at least 50% identity with the sequence YWGQGTQVTVSS (SEQ ID NO:51); or (v) any combination of (i) to (iv).

12. The monovalent antibody of item 11, which comprises:

(i) a FR1 comprising an amino acid sequence having at least 90% identity with the sequence MAEVQLQASGGGFVQPGGSLRLSCAASG (SEQ ID NO:48);

(ii) a FR2 comprising an amino acid sequence having at least 90% identity with the sequence MGWFRQAPGKEREFVSAIS (SEQ ID NO:49);

(iii) a FR3 comprising or consisting of an amino acid sequence having at least 90% identity with the sequence YYADSVKGRFTISRDNSKNTVYLQMNSLRAEDTATYYCA (SEQ ID NO:50);

(iv) a FR4 comprising an amino acid sequence having at least 90% identity with the sequence YWGQGTQVTVSS (SEQ ID NO:51); or (v) any combination of (i) to (iv).

13. The monovalent antibody of item 11, which comprises:

(i) a FR1 comprising the sequence MAEVQLQASGGGFVQPGGSLRLSCAASG (SEQ ID NO:48);

(ii) a FR2 comprising the sequence MGWFRQAPGKEREFVSAIS (SEQ ID NO:49);

(iii) a FR3 comprising the sequence YYADSVKGRFTISRDNSKNTVYLQMNSLRAEDTATYYCA (SEQ ID NO:50);

(iv) a FR4 comprising the sequence YWGQGTQVTVSS (SEQ ID NO:51); or (v) any combination of (i) to (iv).

14. The monovalent antibody of any one of items 1 to 13, comprising an amino acid sequence having at least 80% identity with the sequence set forth in any one of SEQ ID NOs:1-10, 52 and 53.

15. The monovalent antibody of item 14, comprising an amino acid sequence having at least 80% identity with the sequence set forth in any one of SEQ ID NOs:6, 7, 9 and 52.

16. The monovalent antibody of item 15, comprising an amino acid sequence having at least 80% identity with the sequence set forth in SEQ ID NO:6 or 52.

17. The monovalent antibody of item 14, comprising an amino acid sequence having at least 90% identity with the sequence set forth in any one of SEQ ID NOs:1-10, 52 and 53.

18. The monovalent antibody of item 15, comprising an amino acid sequence having at least 90% identity with the sequence set forth in any one of SEQ ID NOs:6, 7, 9 and 52.

19. The monovalent antibody of item 16, comprising an amino acid sequence having at least 90% identity with the sequence set forth in SEQ ID NO:6 or 52.

20. The monovalent antibody of item 17, comprising an amino acid sequence set forth in any one of SEQ ID NOs:1-10, 52 and 53.

21. The monovalent antibody of item 18, comprising an amino acid sequence set forth in any one of SEQ ID NOs:6, 7, 9 and 52.

22. The monovalent antibody of item 19, comprising an amino acid sequence set forth in SEQ ID NO:6 or 52.

23. The monovalent antibody of any one of items 1 to 22, wherein said antibody is conjugated to a label, a nanoparticle, a drug, a peptide, a nucleic acid, a toxin, an enzyme, a radioisotope, or a half-life extending moiety.

24. A nucleic acid comprising a nucleotide sequence encoding the monovalent antibody defined in any one of items 1 to 12.

25. A vector comprising the nucleic acid of item 24.

26. A cell comprising the nucleic acid of item 24 or the vector of item 25.

27. A pharmaceutical composition comprising the monovalent antibody defined in any one of items 1 to 23 and one or more pharmaceutically acceptable carriers, excipient, and/or diluents.

28. A method for binding human galectin-7 (hGAL-7) comprising contacting said hGAL-7 with the monovalent antibody of any one of items 1 to 23 or the composition of item 27.

29. The method of item 29, wherein said galectin-7 is expressed at the surface of a cell.

30. A method for inhibiting galectin-7-mediated apoptosis in a cell, said method comprising contacting said cell with an effective amount of the monovalent antibody of any one of items 4 to 13, 15, 16, 18, 19, 21 and 22, or the composition of item 27.

31. The method of item 30, wherein said cell is an immune cell.

32. The method of item 31, wherein said immune cell is a T lymphocyte.

33. A method for inhibiting the dimerization of human galectin-7 comprising contacting said galectin-7 with the monovalent antibody of any one of items 5, 8 to 13, 16, 19, and 22, or the composition of item 27.

34. The method of item 33, wherein said galectin-7 is expressed at the surface of a cell.

35. A method for treating a galectin-7-expressing cancer in a subject, said method comprising administering to said subject an effective amount of the monovalent antibody of any one of items 1 to 23 or the composition of item 27.

36. The method of item 35, wherein the cancer is of epithelial origin.

37. The method of item 35 or 36, wherein the cancer is a breast cancer, a melanoma, an ovarian cancer or a lymphoma.

38. The method of any one of items 35 to 37, wherein said monovalent antibody or composition of item 17 is administered in combination with a second anti-tumoral agent.

39. A method for treating an eye disease or condition associated with pathological neovascularization or angiogenesis.

40. The method of item 39, wherein the eye disease or condition is trachoma, corneal ulcer, keratoconjunctivitis, keratitis, chemical burn, ocular histoplasmosis, pathologic myopia, proliferative diabetic retinopathy, age-related macular degeneration, or retinopathy of prematurity.

41. The method of any one of items 35 to 40, wherein the subject is a human subject.

42. The monovalent antibody of any one of items 1 to 23, or the composition of item 27, for use in binding human galectin-7 (hGAL-7).

43. The monovalent antibody or composition for use according to item 42, wherein said galectin-7 is expressed at the surface of a cell.

44. The monovalent antibody of any one of items 4 to 13, 15, 16, 18, 19, 21 and 22, or the composition of item 27, for use in inhibiting galectin-7-mediated apoptosis in a cell.

45. The monovalent antibody or composition for use according to item 44, wherein said cell is an immune cell.

46. The monovalent antibody or composition for use according to item 45, wherein said immune cell is a T lymphocyte.

47. The monovalent antibody of any one of items 5, 8 to 13, 16, 19, and 22, or the composition of item 27, for inhibiting the dimerization of human galectin-7.

48. The monovalent antibody or composition for use according to item 47, wherein said galectin-7 is expressed at the surface of a cell.

49. The monovalent antibody of any one of items 1 to 23, or the composition of item 27, for use in the treatment of a galectin-7-expressing cancer in a subject.

50. The monovalent antibody or composition for use according to item 49, wherein the cancer is of epithelial origin.

51. The monovalent antibody or composition for use according to item 49 or 50, wherein the cancer is a breast cancer, a melanoma, an ovarian cancer or a lymphoma.

52. The monovalent antibody or composition for use according to any one of items 49 to 51, wherein said monovalent antibody or composition is used in combination with a second anti-tumoral agent.

53. The monovalent antibody of any one of items 1 to 23, or the composition of item 27, for use in the treatment of an eye disease or condition associated with pathological neovascularization or angiogenesis.

54. The monovalent antibody or composition for use according to item 53, wherein the eye disease or condition is trachoma, corneal ulcers, keratoconjunctivitis, keratitis, chemical burns, ocular histoplasmosis, pathologic myopia, proliferative diabetic retinopathy, age-related macular degeneration (AMD), or retinopathy of prematurity.

55. The monovalent antibody or composition for use according to any one of items 49 to 54, wherein the subject is a human subject.

56. Use of the monovalent antibody of any one of items 1 to 23, or the composition of item 27, for the manufacture of a medicament for binding human galectin-7.

57. The use according to item 56, wherein said galectin-7 is expressed at the surface of a cell.

58. Use of the monovalent antibody of any one of items 4 to 13, 15, 16, 18, 19, 21 and 22, or the composition of item 27, for the manufacture of a medicament for inhibiting galectin-7-mediated apoptosis in a cell.

59. The use according to item 56, wherein said cell is an immune cell.

60. The use according to item 57, wherein said immune cell is a T lymphocyte.

61. Use of the monovalent antibody of any one of items 5, 8 to 13, 16, 19, and 22, or the composition of item 27, for the manufacture of a medicament for inhibiting the dimerization of human galectin-7.

62. The use according to item 61, wherein said galectin-7 is expressed at the surface of a cell.

63. Use of the monovalent antibody of any one of items 1 to 23, or the composition of item 27, for the manufacture of a medicament for the treatment of a galectin-7-expressing cancer in a subject.

64. The use according to item 63, wherein the cancer is of epithelial origin.

65. The use according to item 63 or 64, wherein the cancer is a breast cancer, a melanoma, an ovarian cancer or a lymphoma.

66. The use according to any one of items 63 to 65, wherein said monovalent antibody or composition is used in combination with a second anti-tumoral agent.

67. Use of the monovalent antibody of any one of items 1 to 23, or the composition of item 27, for the manufacture of a medicament for the treatment of an eye disease or condition associated with pathological neovascularization or angiogenesis.

68. The use according to item 67, wherein the eye disease or condition is trachoma, corneal ulcer, keratoconjunctivitis, keratitis, chemical burn, ocular histoplasmosis, pathologic myopia, proliferative diabetic retinopathy, age-related macular degeneration, or retinopathy of prematurity.

69. The use according to any one of items 63 to 68, wherein the subject is a human subject.

70. A method for detecting a human galectin-7-expressing cell comprising contacting said cell with the monovalent antibody of any one of items 1 to 23.

71. The method of item 70, wherein said monovalent antibody is conjugated to a detectable label.

72. The method of item 71, wherein said detectable label is a fluorescent molecule or a radioisotope.

73. The method of any one of items 70 to 72, wherein said cell is a tumor cell.

74. The method of item 73, wherein said method is for diagnosing and/or monitoring the progression of a galectin-7-positive cancer in a subject.

75. Use of the monovalent antibody of any one of items 1 to 23 for detecting a human galectin-7-expressing cell.

76. The use of item 75, wherein said monovalent antibody is conjugated to a detectable label.

77. The use of item 76, wherein said detectable label is a fluorescent molecule or a radioisotope.

78. The use of any one of items 75 to 77, wherein said cell is a tumor cell.

79. The use of item 78, wherein said use is for diagnosing and/or monitoring the progression of a galectin-7-positive cancer in a subject.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 3A-B shows the identification of 12 GAL-7-specific nanobodies. Phage nanobody selection was carried out using stringent conditions with hybrigenics non-immune library. FIG. 3A is a histogram showing the validation of hGAL-7 specificity of each nanobody obtained by ELISA using His-tagged myelin basic protein (MBP) as control. The clones were sequenced, converted to amino acid and aligned (FIG. 3B). The complementary determining regions (CDRs) that make up the binding paratope and located between the framework regions (FRs) 1-4 are shown. Reference is a nanobody with CDR region replaced by "X".

DISCLOSURE OF INVENTION

The use of the terms "a" and "an" and "the" and similar referents in the context of describing the invention are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language ("e.g.", "such as", etc.) provided herein, is intended merely to better illustrate the invention and does not pose a limitation on the scope of the invention unless otherwise claimed.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

Unless otherwise defined, all technical and scientific terms used herein have the same meaning as commonly understood by one of ordinary skill in the art to which this invention belongs.

Any and all combinations and subcombinations of the embodiments and features disclosed herein are encompassed by the present disclosure.

Figure 1:
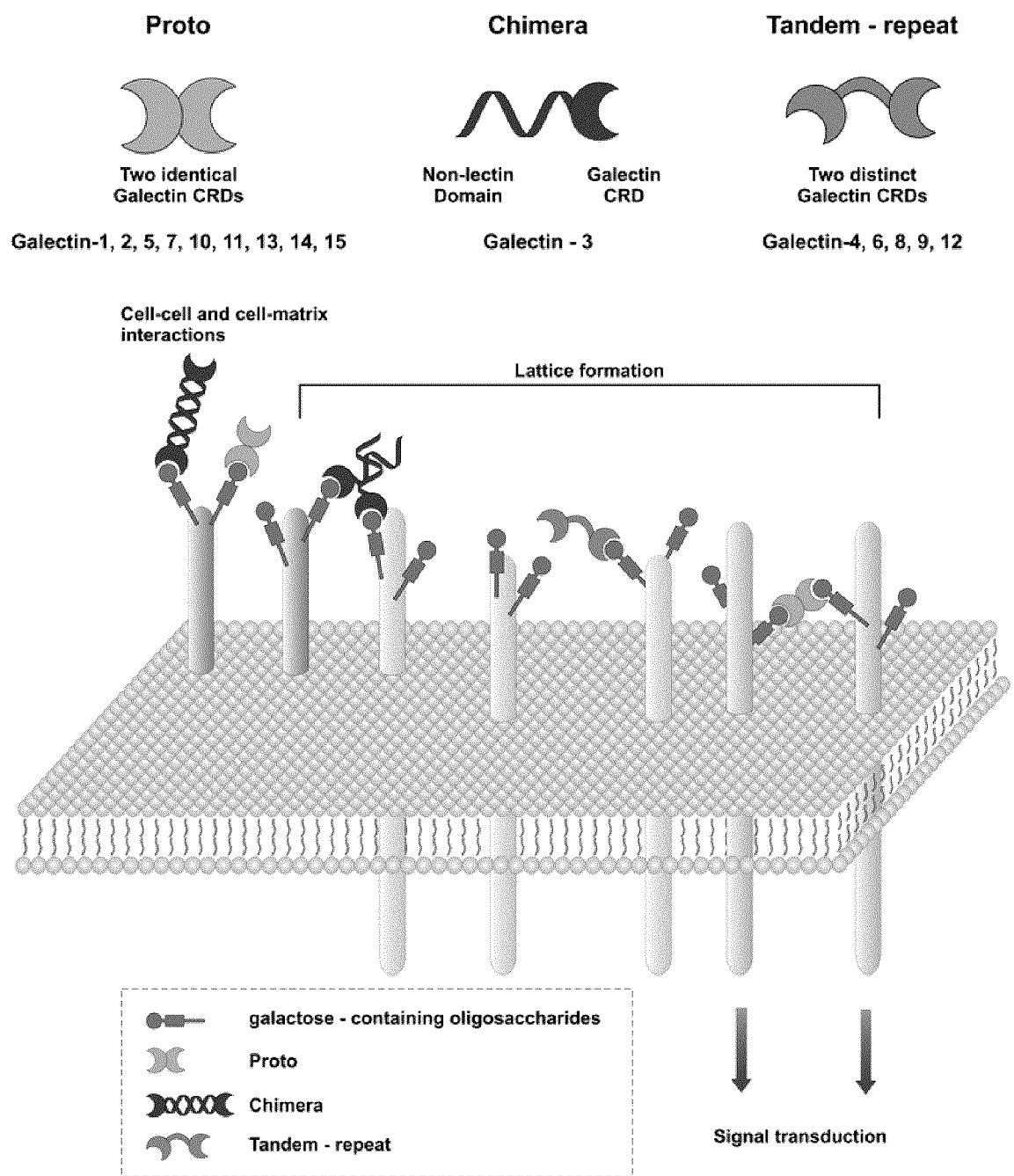
FIG. 1 shows the structure of galectins. Top panel: Schematic diagrams of galectin structures. Galectins are a family of glycan binding lectins that recognize carbohydrates by conserved carbohydrate-recognition domains (CRDs). The 15 galectins that have been identified in mammals are widely distributed and have multiple roles in innate and adaptive immune responses and have been implicated in the pathogenesis of inflammatory, autoimmune and malignant disorders. Galectins are classified on the basis of their structure into three groups: prototypical galectins that contain one CRD (Galectin-1, 2, 5, 7, 10, 11, 13, 14 and 15); Galectin-3, a chimeric galectin which consists of one CRD covalently linked to tandem repeats of proline- and glycine-rich short domains; and tandem repeat galectins that contain two covalently linked CRDs connected by a small peptide domain of up to 70 aa (Galectin-4, 6, 8, 9 and 12). Lower panel: Prototypical galectins exist as dimers. Galectin-3 can both dimerize and oligomerize when it binds to multivalent carbohydrate chains, while tandem repeat galectins have two carbohydrate-binding sites. Galectins interact with transmembrane glycoconjugates and trigger intracellular signaling events; they can also bridge two cells or cells to extracellular matrix proteins and can be secreted in the extracellular space.
Figure 2:
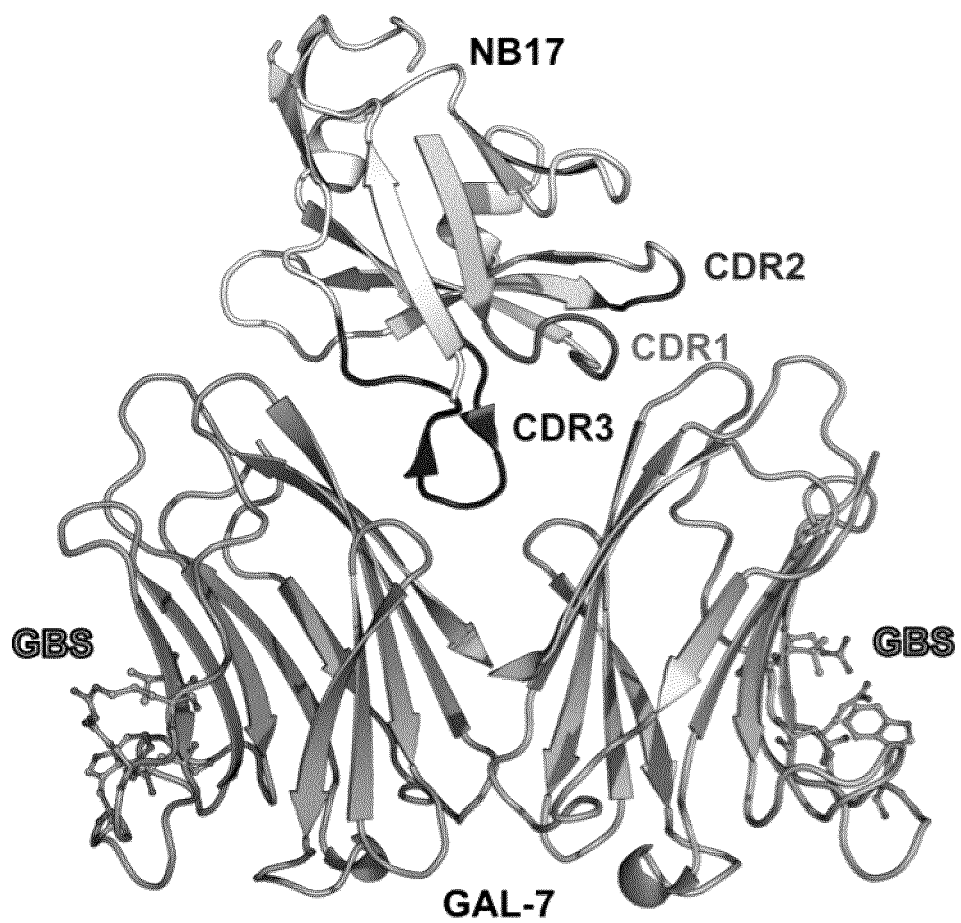
FIG. 2 shows the manual docking of the NB17 camelid nanobody on the GAL-7 homodimer. Hypothetical binding of NB17 (PDB 4ZG1) on GAL-7 (PDB 4GAL). NB17's CDR3 protrudes out of the NB17 protein core to allow potential site-specific interaction at the homodimeric interface of GAL-7.

In the studies described herein, the present inventors have developed cameloid antibodies (nanobodies, Nbs, also called single domain $V_{HH}$ antibodies), which are particularly well-suited for dimer-interference. First, Nbs bind antigenic epitopes by virtue of a single (monovalent) and variable domain encoded in the heavy chain fragment [Hamers-Casterman et al., 2013]. This is an important issue in the case of galectin because in contrast to conventional (multivalent) antibodies (Abs), binding of monovalent Nbs on galectin-bound cell surface glycoreceptors cannot trigger intracellular signals induced by cross-linking of glycoreceptors. Secondly, Nbs can recognize epitopes that may be inaccessible to conventional Abs because of their extended convex-shaped paratope. This is possible because the hypervariable region of Nbs is made of a single stretch of amino acids (a.a.) composed of flexible peptide loops, including a relatively long complementary determining region (CDR)-3 loop that is extended and made of 17 a.a on average (compared to 12 a.a. in humans). This confers Nbs with a unique antigen-binding mode capable of targeting hidden (poorly immunogenic) epitopes. The structure of their antigen-binding region is thus ideally suited for targeting epitopes buried at the dimer interface of GAL-7 (FIG. 2). Finally, Nbs, like conventional Abs, usually have high affinity for their ligands.

Accordingly, in a first aspect, the present disclosure provides a monovalent antibody that specifically binds to human GAL-7. In an embodiment, the present disclosure provides a monovalent antibody that specifically binds to the dimer interface of hGAL-7. In an embodiment, the monovalent antibody inhibits or interferes with human GAL-7 homodimerization. In another embodiment, the monovalent antibody inhibits or interferes with human GAL-7 activity, for example GAL-7-induced killing of cells such as human activated T cells.

The term "monovalent antibody" refers to an antibody that comprises a single monomeric variable antibody domain, and thus a single set of complementary determining regions (CDRs). Examples of monovalent antibodies include single-domain antibodies (sdAbs, also called nanobodies), camelid antibodies (e.g., from dromedaries, camels, llamas, alpacas), $V_H H$ fragments and $V_{NAR}$ fragments. In an embodiment, the monovalent antibody is a nanobody. Single domain antibodies may be derived from any species including mouse, human, camel, llama, goat, rabbit, and bovine. For example, naturally occurring $V_H H$ molecules can be derived from antibodies raised in Camelidae species, for example in camel, dromedary, alpaca and guanaco. Synthetic $V_H H$ molecules may also be identified/generated using library of humanized nanobodies (see, e.g., Moutel et al., eLife 2016; 5:e16228; Salema et al., MAbs vol. 8, No. 7, 1286-1301; Gene, R W et al., (2015) J Immunol Methods 416, 29-39; Kumaran, J. (2012). Methods Mol Biol 911, 105-124).

Human GAL-7 is a 15 kDa prototype galectin with a single CRD, monomeric but capable of dimerization in solution. It was first reported in an effort to identify markers of keratinocyte differentiation. GAL-7 involvement in the maintenance of the pluri-stratified epithelia and epidermal stratification has highlighted its role in wound healing. It was proven to be an efficient growth factor with therapeutic implications. Some of the more recent advances on GAL-7 have shown its implication in apoptosis induction in various types of cell. GAL-7 expression is induced upon UV radiation and regulated by p53, therefore showing high levels in certain types of cancer. hGAL-7 has attracted more interest in cancer because its preferential expression in epithelial tissues and carcinoma, it is found in the nucleus of many cancer cells, including hypopharyngeal (HSCCs) and laryngeal (LSCCs) squamous cell carcinomas tissues, colon carcinoma cells (DLD-1), cervical adenocarcinoma (HeLa), epithelial ovarian cancer tissues and oral epithelial dysplasia tissues (Saussez S et al. Histopathology 52: 483-493, 2008; Kuwabara I et al. J Biol Chem 277: 3487-3497, 2002; Kim H J et al. Anticancer Res 33: 1555-1561, 2013; de Vasconcelos Carvalho M et al. J Oral Pathol Med 42: 174-179, 2013). GAL-7 is also observed in the cytosol of colon carcinoma cell line (DLD-1), cervical adenocarcinoma cells (HeLa), epithelial ovarian cancer and oral epithelial dysplasia tissues, (Uhlen M et al. Nat Biotechnol 28: 1248-1250, 2010; Kuwabara I, et al. J Biol Chem 277: 3487-3497, 2002; Kim H J et al. Anticancer Res 33: 1555-1561, 2013; de Vasconcelos Carvalho M, et al. J Oral Pathol Med 42: 174-179, 2013). It is also detected in mitochondrial fractions, most notably in the case of human colorectal carcinoma and cervical adenocarcinoma cell lines (HCT116, HeLa) and the HaCaT keratinocyte cell line (Villeneuve C et al., Mol Biol Cell 22: 999-1013, 2011). GAL-7 has been shown to be involved in cancer development, for example in the growth stimulation of lymphomas (Moisan S, et al., Leukemia. 2003; 17:751-759; Demers M, et al., Cancer Res. 2005; 65:5205-5210) and the invasive behavior of ovarian cancer cells (Labrie, M., et al., Oncotarget, 2014. 5(17): p. 7705-21). GAL-7 was also described as a key element in aggressive metastasis following its overexpression in breast carcinomas (Demers M, et al., Am J Pathol. 2010; 176:3023-3031), and thus represents a potential therapeutic target. GAL-7 has also been shown in the neovascularization process in the eye (Cao et al., Arch Ophthalmol. 2003 January; 121(1):82-6), and thus inhibition of GAL-7 may be useful for the treatment of eye diseases or conditions associated with pathological neovascularization/angiogenesis (ocular neovascularization), such as trachoma, corneal ulcers, keratoconjunctivitis (e.g., phlyctenular keratoconjunctivitis), keratitis (e.g., rosacea keratitis, interstitial keratitis, sclerosing keratitis), burns (e.g., chemical burns), ocular histoplasmosis, pathologic myopia, proliferative diabetic retinopathy, age-related macular degeneration (AMD), and retinopathy of prematurity.

In an embodiment, the monovalent antibody disclosed herein may be used for the treatment of any of the diseases/cancers defined above.

In an embodiment, the monovalent antibody comprises one of the following combinations of complementarity determining regions (CDRs):
  (a) a CDR1 comprising or consisting of an amino acid sequence having at least 80%, 85% or 90% identity with the sequence AGSRSDV; a CDR2 comprising or consisting of an amino acid sequence having at least 80%, 85% or 90% identity with the sequence GFWGWTT; and a CDR3 comprising or consisting of an amino acid sequence having at least 80%, 85% or 90% identity with the sequence LGGAPGQTG;
  (b) a CDR1 comprising or consisting of an amino acid sequence having at least 80%, 85% or 90% identity with the sequence DTSRFDV; a CDR2 comprising or consisting of an amino acid sequence having at least 80%, 85% or 90% identity with the sequence WWSS-DHI; and a CDR3 comprising or consisting of an amino acid sequence having at least 80%, 85% or 90% identity with the sequence YGEYPPRMNRRP;
  (c) a CDR1 comprising or consisting of an amino acid sequence having at least 80%, 85% or 90% identity with the sequence TTSNSSG; a CDR2 comprising or consisting of an amino acid sequence having at least 80%, 85% or 90% identity with the sequence WDHGILT; and a CDR3 comprising or consisting of an amino acid sequence having at least 80%, 85% or 90% identity with the sequence HGYVHFNMTHRHISD;

(d) a CDR1 comprising or consisting of an amino acid sequence having at least 80%, 85% or 90% identity with the sequence TTSNGEV; a CDR2 comprising or consisting of an amino acid sequence having at least 80%, 85% or 90% identity with the sequence FGAGSSE; and a CDR3 comprising or consisting of an amino acid sequence having at least 80%, 85% or 90% identity with the sequence ASWYHSSIGSMS;

(e) a CDR1 comprising or consisting of an amino acid sequence having at least 80%, 85% or 90% identity with the sequence AYSFESG; a CDR2 comprising or consisting of an amino acid sequence having at least 80%, 85% or 90% identity with the sequence SDADLFS; and a CDR3 comprising or consisting of an amino acid sequence having at least 80%, 85% or 90% identity with the sequence AFSSGGELS;

(f) a CDR1 comprising or consisting of an amino acid sequence having at least 80%, 85% or 90% identity with the sequence RYSRIEI; a CDR2 comprising or consisting of an amino acid sequence having at least 80%, 85% or 90% identity with the sequence STPSSNE; and a CDR3 comprising or consisting of an amino acid sequence having at least 80%, 85% or 90% identity with the sequence RWDWHSWDT;

(g) a CDR1 comprising or consisting of an amino acid sequence having at least 80%, 85% or 90% identity with the sequence STSYSST; a CDR2 comprising or consisting of an amino acid sequence having at least 80%, 85% or 90% identity with the sequence FDGTSKP; and a CDR3 comprising or consisting of an amino acid sequence having at least 80%, 85% or 90% identity with the sequence AGEWEALMWPPVHDFWIY;

(h) a CDR1 comprising or consisting of an amino acid sequence having at least 80%, 85% or 90% identity with the sequence RTSSQDI; a CDR2 comprising or consisting of an amino acid sequence having at least 80%, 85% or 90% identity with the sequence DYSGGNV; and a CDR3 comprising or consisting of an amino acid sequence having at least 80%, 85% or 90% identity with the sequence FLGEEKTSW;

(i) a CDR1 comprising or consisting of an amino acid sequence having at least 80%, 85% or 90% identity with the sequence STSYGET; a CDR2 comprising or consisting of an amino acid sequence having at least 80%, 85% or 90% identity with the sequence YYSTRKP; and a CDR3 comprising or consisting of an amino acid sequence having at least 80%, 85% or 90% identity with the sequence IVAYIYADGVRGYHQKID;

(j) a CDR1 comprising or consisting of an amino acid sequence having at least 80%, 85% or 90% identity with the sequence GGYDWDA; a CDR2 comprising or consisting of an amino acid sequence having at least 80%, 85% or 90% identity with the sequence SNNNGSR; and a CDR3 comprising or consisting of an amino acid sequence having at least 80%, 85% or 90% identity with the sequence ADQ;

(k) a CDR1 comprising or consisting of an amino acid sequence having at least 80%, 85% or 90% identity with the sequence TYSSIEV; a CDR2 comprising or consisting of an amino acid sequence having at least 80%, 85% or 90% identity with the sequence FEPNEFA; and a CDR3 comprising or consisting of an amino acid sequence having at least 80%, 85% or 90% identity with the sequence SSVEWRQNGKPNTAS; or (l) a CDR1 comprising or consisting of an amino acid sequence having at least 80%, 85% or 90% identity with the sequence DTSESTS; a CDR2 comprising or consisting of an amino acid sequence having at least 80%, 85% or 90% identity with the sequence RSSTWDA; and a CDR3 comprising or consisting of an amino acid sequence having at least 80%, 85% or 90% identity with the sequence MADIFDHPQNASFMK.

Although it will be appreciated that the skilled person will be able to provide for various single-domain antibodies based on the various CDR1, CDR2, CDR3 as disclosed herein, as well as the other sequences provided (including the various framework sequences and the full-length sequence of the single-domain antibodies), preferably the single-domain antibody has a CDR1, CDR2 and a CDR3 as shown in combination in FIG. 3B, and conservative sequence variants thereof. In other words, a single-domain antibody according to the present disclosure preferably comprises the CDR1 and the CDR2 and the CDR3 shown in FIG. 3B. As will be appreciated by the skilled person, also included are conservative sequence variants of the CDR1, CDR2 and CDR3 combinations as disclosed in FIG. 3B. These amino acid changes can typically be made without altering the biological activity, function, or other desired property of the antibody, such as its affinity or its specificity for antigen. In general, single amino acid substitutions in nonessential regions of an antibody do not substantially alter biological activity. Furthermore, substitutions of amino acids that are similar in structure or function are less likely to disrupt the antibody's biological activity. One or more of the CDRs may be mutated to increase the affinity and/or specificity of the monovalent antibody for hGAL-7, e.g., to generate an affinity-matured monovalent antibody.

In an embodiment, one or two residues in the above-noted CDRs sequences are substituted. In a further embodiment, one residue in the above-noted CDRs sequences is substituted.

In a further embodiment, the monovalent antibody comprises one of the following combinations of CDRs:

(a) a CDR1 comprising or consisting of the amino acid sequence AGSRSDV; a CDR2 comprising or consisting of the amino acid sequence GFWGWTT; and a CDR3 comprising or consisting of the amino acid sequence LGGAPGQTG;

(b) a CDR1 comprising or consisting of the amino acid sequence DTSRFDV; a CDR2 comprising or consisting of the amino acid sequence WWSSDHI; and a CDR3 comprising or consisting of the amino acid sequence YGEYPPRMNRRP;

(c) a CDR1 comprising or consisting of the amino acid sequence TTSNSSG; a CDR2 comprising or consisting of the amino acid sequence WDHGILT; and a CDR3 comprising or consisting of the amino acid sequence HGYVHFNMTHRHISD;

(d) a CDR1 comprising or consisting of the amino acid sequence TTSNGEV; a CDR2 comprising or consisting of the amino acid sequence FGAGSSE; and a CDR3 comprising or consisting of the amino acid sequence ASWYHSSIGSMS;

(e) a CDR1 comprising or consisting of the amino acid sequence AYSFESG; a CDR2 comprising or consisting of the amino acid sequence SDADLFS; and a CDR3 comprising or consisting of the amino acid sequence AFSSGGELS;

(f) a CDR1 comprising or consisting of the amino acid sequence RYSRIEI; a CDR2 comprising or consisting of the amino acid sequence STPSSNE; and a CDR3 comprising or consisting of the amino acid sequence RWDWHSWDT;

(g) a CDR1 comprising or consisting of the amino acid sequence STSYSST; a CDR2 comprising or consisting of the amino acid sequence FDGTSKP; and a CDR3 comprising or consisting of the amino acid sequence AGEWEALMWPPVHDFWIY;

(h) a CDR1 comprising or consisting of the amino acid sequence RTSSQDI; a CDR2 comprising or consisting of the amino acid sequence DYSGGNV; and a CDR3 comprising or consisting the amino acid sequence FLGEEKTSW;

(i) a CDR1 comprising or consisting of the amino acid sequence STSYGET; a CDR2 comprising or consisting of the amino acid sequence YYSTRKP; and a CDR3 comprising or consisting of the amino acid sequence IVAYIYADGVRGYHQKID;

(j) a CDR1 comprising or consisting of the amino acid sequence GGYDWDA; a CDR2 comprising or consisting of the amino acid sequence SNNNGSR; and a CDR3 comprising or consisting of the amino acid sequence ADQ;

(k) a CDR1 comprising or consisting of the amino acid sequence TYSSIEV; a CDR2 comprising or consisting of the amino acid sequence FEPNEFA; and a CDR3 comprising or consisting of the amino acid sequence SSVEWRQNGKPNTAS; or (l) a CDR1 comprising or consisting of the amino acid sequence DTSESTS; a CDR2 comprising or consisting of the amino acid sequence RSSTWDA; and a CDR3 comprising or consisting of the amino acid sequence MADIFDHPQNASFMK.

In a preferred embodiment, the monovalent antibody comprises the combination of CDRs defined in item (f), (g), (i) or (k) above, and more preferably the monovalent antibody comprises the combination of CDRs defined in item (f) or (k) above. In an embodiment, the monovalent antibody comprises the combination of CDRs defined in item (f) above. In an embodiment, the monovalent antibody comprises the combination of CDRs defined in item (k) above.

In an embodiment, the monovalent antibody comprises: (i) a framework region (FR) 1 comprising or consisting of an amino acid sequence having at least 50%, 60%, 70%, 75%, 80%, 85%, 90% or 95% identity with the sequence MAEVQLQASGGGFVQPGGSLRLSCAASG; (ii) a FR2 comprising or consisting of an amino acid sequence having at least 50%, 60%, 70%, 75%, 80%, 85%, 90% or 95% identity with the sequence MGWFRQAPGKEREFVSAIS; (iii) a FR3 comprising or consisting of an amino acid sequence having at least 50%, 60%, 70%, 75%, 80%, 85%, 90% or 95% identity with the sequence YYADSVKGRFTISRDNSKNTVYLQMNSLRAED-TATYYCA; (iv) a FR4 comprising or consisting of an amino acid sequence having at least 50%, 60%, 70%, 75%, 80%, 85%, 90% or 95% identity with the sequence YWGQGTQVTVSS; or (v) any combination of (i) to (iv).

In an embodiment, the monovalent antibody comprises or consists of an amino acid sequence having at least 80%, 85%, 90%, 95%, 96%, 97%, 98% or 99% identity with one of the sequences set forth in FIG. 3B (SEQ ID Nos: 1-10, 52 or 53), preferably with one of the sequences set forth in SEQ ID Nos: 6, 7, 9 and 52, and more preferably with the sequences set forth in SEQ ID No:6 or 52. In a further embodiment, the monovalent antibody comprises or consists of one of the sequences set forth in FIG. 3B (SEQ ID Nos: 1-10, 52 or 53), preferably the sequences set forth in SEQ ID Nos: 6, 7, 9 and 52, and more preferably the sequences set forth in SEQ ID No:6 or 52.

Variations in the monovalent antibody described herein, can be made, for example, using any of the techniques and guidelines for conservative and non-conservative mutations set forth, for instance, in U.S. Pat. No. 5,364,934. Variations may be a substitution, deletion or insertion of one or more codons encoding the monovalent antibody that results in a change in the amino acid sequence as compared with the native sequence antibody. Optionally the variation is by substitution of at least one amino acid with any other amino acid (including naturally occurring amino acids as well as amino acid analogs) in one or more of the domains of the monovalent antibody. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting monovalent antibody variants for activity exhibited by the "native" (or reference) monovalent antibody.

"Identity" refers to sequence identity between two polypeptides. Identity can be determined by comparing each position in the aligned sequences. Methods of determining percent identity are known in the art, and several tools and programs are available to align amino acid sequences and determine a percentage of identity including EMBOSS Needle, ClustalW, SIM, DIALIGN, etc. As used herein, a given percentage of identity with respect to a specified subject sequence, or a specified portion thereof, may be defined as the percentage of amino acids in the candidate derivative sequence identical with the amino acids in the subject sequence (or specified portion thereof), after aligning the sequences and introducing gaps, if necessary to achieve the maximum percent sequence identity, as generated by the Smith Waterman algorithm (Smith & Waterman, *J. Mol. Biol.* 147 147: 195-7 (1981)) using the BLOSUM substitution matrices (Henikoff & Henikoff, *Proc. Natl. Acad. Sci. USA* 89:10915-9 (1992)) as similarity measures. A "% identity value" is determined by the number of matching identical amino acids divided by the sequence length for which the percent identity is being reported.

In an embodiment, the monovalent antibodies of the present disclosure may be subjected to in vitro affinity maturation. A library comprising variants of the monovalent antibodies disclosed herein may be generated and screened to identity monovalent antibodies having improved affinity and/or specificity for the target antigen (hGAL-7). Thus, in another aspect, the present disclosure provides a method for identifying affinity-matured monovalent antibodies specific for hGAL-7 comprising: (i) generating a library of test monovalent antibodies, wherein said test monovalent antibodies comprises one or more mutations (point mutations, substitutions) relative to one of the parent monovalent antibodies disclosed herein (FIG. 3); (ii) selecting the monovalent antibodies that binds to hGAL-7 with higher affinity than the parent monovalent antibody, thereby identifying affinity-matured antibodies. In an embodiment, the one or more mutations is in one or more of the CDRs disclosed herein. In an embodiment, the test monovalent antibody comprises 15 mutations or less relative to the parent monovalent antibody. In an embodiment, the test monovalent antibody comprises 10 mutations or less relative to the parent monovalent antibody. In embodiments, the test monovalent antibody comprises 9, 8, 7, 6, or 5 mutations or less relative to the parent monovalent antibody. In an embodiment, the affinity of the affinity-matured monovalent antibody for hGAL-7 is at least 2-fold that of the parent monovalent antibody. In embodiments, the affinity of the affinity-matured monovalent antibody for hGAL-7 is at least 5-, 10-, 20-, 50- or 100-fold that of the parent monovalent antibody.

Modifications to the C or N-terminal $V_H$ framework sequence may be made to the monovalent antibodies of the disclosure to improve their properties. For example, the $V_H$ domain may comprise C or N-terminal extensions or deletions. C-terminal extensions can be added to the C terminal end of a $V_H$ domain.

In one embodiment, the monovalent antibodies of the disclosure comprise C-terminal extensions or deletions of from 1 to 50, or more residues, for example 1 to 25, e.g., 1, 2, 3, 4, 5, 6, 7, 8, 9 or 10 additional amino acids.

Additional C or N-terminal residues can be linkers that are used to conjugate the monovalent antibodies of the disclosure to another moiety, or tags that facilitate the detection of the molecule (hGAL-7). Such tags are well known in the art and include for example polyhistidine tags (His-tags), polyarginine tags, polyaspartate tags, polycysteine tags, polyphenylalanine tags, glutathione S-transferase (GST) tags, Maltose binding protein (MBP) tags, calmodulin binding peptide (CBP) tags, Streptavidin/Biotin-based tags, HaloTag®, Profinity eXact® tags, epitope tags (such as FLAG, hemagglutinin (HA), HSV, S/S1, c-myc, KT3, T7, V5, E2, and Glu-Glu epitope tags), reporter tags such as β-galactosidase (β-gal), alkaline phosphatase (AP), chloramphenicol acetyl transferase (CAT), and horseradish peroxidase (HRP) tags (see, e.g., Kimple et al., *Curr Protoc Protein Sci.* 2013; 73: Unit-9.9).

The monovalent antibody according to the present disclosure may comprise at least one constant domain, e.g., a constant domain of a light and/or heavy chain, or a fragment thereof. For example, the monovalent antibody may comprise a Fragment crystallizable (Fc) region or domain of the constant heavy chain of an antibody. The Fc fragment may comprise two or three constant domains, e.g., a $CH_2$ domain and $CH_3$ domain. The Fc region may be obtained from a human IgG1, a human IgG4, or a variant of a human IgG1 or IgG4 having up to ten amino acid modifications, for example. In an embodiment, the Fc fragment comprises or consists of the $CH_2$ domain and $CH_3$ domain of a human antibody, preferably a human IgG such as IgG1. The presence of an Fc domain on the monovalent antibody may promote antibody-dependent cellular cytotoxicity (ADCC), i.e. the cytotoxic killing of cells bound by the monovalent antibody (e.g., GAL-7-expressing tumor cells).

The monovalent antibody according to the present disclosure may be linked to other function or non-functional groups, for example the monovalent antibody may be conjugated to a label (e.g., a biotin label, a fluorescent label, an enzyme label, a coenzyme label, a chemiluminescent label), a nanoparticle, a drug (e.g., a chemotherapeutic agent, an anti-inflammatory drug), a peptide, a nucleic acid, a toxin, an enzyme, a radioisotope, a half-life extending moiety (e.g., PEGylation, using a serum albumin protein), a therapeutic molecule or any other chemical moiety. The monovalent antibody may be used to target hGAL-7 expressing cells (e.g., cancer cells), or may be used to detect hGAL-7 and/or cells expressing hGAL-7, in diagnostic, prognostic, disease monitoring and medical imaging applications (see, e.g., Jailkhani et al., *PNAS*, 116(28): 14181-14190; Hu et al. (2017), *Front. Immunol.* 8:1442; Virant et al., (2018) 9:930).

In an embodiment, the monovalent antibody according to the present disclosure is conjugated to one or more therapeutic or active agents (e.g., a drug), and thus may also be used therapeutically to deliver the therapeutic agent(s) (e.g., anti-tumor agent or any other agent useful for the treatment of the disease or condition or for relieving one or more symptoms) into a cell or tissue, such as a tumor. Any method known in the art for conjugating the monovalent antibody thereof to another moiety (e.g., detectable moiety, active agent) may be employed (Hermanson, *Bioconjugate Techniques*, 3rd edition, 2013, Academic Press, Inc., San Diego).

Nanobodies may be produced in various expression systems including *E. coli*, yeasts, or filamentous fungi (see, for example, Harmsen and De Haard, *Appl Microbiol Biotechnol.* 2007 November; 77(1): 13-22).

A further aspect of the present disclosure provides nucleic acids encoding the monovalent antibody according to the present disclosure. The isolated nucleic acid may be a synthetic DNA, a non-naturally occurring mRNA, or a cDNA, for example. The nucleic acid may be inserted within a plasmid, vector, or transcription or expression cassette. The nucleic acids encoding the monovalent antibody according to the present disclosure may be made and the expressed antibodies may be tested using conventional techniques well known in the art.

In another aspect, the present invention provides a cell, for example a recombinant host cell, comprising the above-noted nucleic acids and expressing the monovalent antibody according to the present disclosure. Methods of preparing monovalent antibodies comprise expressing the encoding nucleic acid(s) in a host cell under conditions to produce the antibodies, and recovering the antibodies. The process of recovering the antibodies may comprise isolation and/or purification of the antibodies. The method of production may comprise formulating the antibodies into a composition including at least one additional component, such as a pharmaceutically acceptable excipient.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred enkaryotic cells include protist, fungal, plant and animal cells. Most preferably host cells include but are not limited to the prokaryotic cell line *E. Coli*; mammalian cell lines CHO, HEK 293 and COS; the insect cell line Sf9; the fungal cell *Saccharomyces cerevisiae*, plant cells, or algae cells.

In another embodiment, the host cell is an immune cell. The anti-hGAL-7 monovalent antibody described herein may be used as a chimeric antigen receptor (CAR) to produce CAR T cells, CAR NK cells, etc. CAR combines a ligand-binding domain (e.g. antibody or antibody fragment) that provides specificity for a desired antigen (e.g., hGAL-7) with an activating intracellular domain (or signal transducing domain) portion, such as a T cell or NK cell activating domain, providing a primary activation signal. Nanobodies capable of binding to molecules expressed by tumor cells are commonly used as CAR. Thus, in another aspect, the present disclosure provides a host cell, preferably an immune cell such as a T cell or NK cell, expressing the monovalent antibody described herein.

The CAR of the present disclosure may also comprise a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, CD28, CD3-epsilon, CD45, CD4, CD5, CD8, CD9, CD16, CD22, CD33, CD37, CD64, CD80, CD86, CD134, CD137, ICOS, CD 154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. In preferred embodiments, the transmembrane domain is derived from CD28 or CD8, which give good receptor stability.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for Syk/ZAP70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d.

The CAR of the present disclosure may also comprise one or more co-stimulatory domains such as human CD28, 4-1BB (CD137), ICOS-1, CD27, OX40 (CD137), DAP10, and GITR (AITR). In embodiment, the CAR is a third generation and comprises two co-stimulating domains such as CD28 and 4-1BB.

The CAR of the present disclosure may also comprise a signal peptide N-terminal to the anti-GAL-7 monovalent antibody described herein so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present disclosure may comprise a spacer sequence as a hinge to connect the anti-GAL-7 monovalent antibody described herein with the transmembrane domain and spatially separate antigen binding domain from the endodomain. A flexible spacer allows to the binding domain to orient in different directions to enable its binding to the desired antigen (e.g., GAL-7). The spacer sequence may, for example, comprise an IgG1 Fc region, an IgG1 hinge or a CD8 stalk, or a combination thereof.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome.

Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the invention is integrated into the genome, e.g., chromosome, of the host cell. Integration may be promoted by inclusion of sequences that promote recombination with the genome, in accordance with standard techniques.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, mouse melanoma cells, rat myeloma cells, human embryonic kidney cells, e.g., HEK293 cells, human embryonic retina cells, and many others. The expression of antibodies and antibody fragments in prokaryotic cells, such as E. coli, is well established in the art. For a review, see for example, Pliickthun Bio/Technology 9: 545-551 (1991). Expression in cultured eukaryotic cells is also available to those skilled in the art, as reviewed in Andersen et al. (2002) *Curr. Opin. Biotechnol.* 13: 117-23, for example.

In another aspect, the present disclosure provides a composition (e.g., a pharmaceutical composition) comprising the above-mentioned monovalent antibody. In an embodiment, the composition further comprises one or more pharmaceutically acceptable carriers, excipient, and/or diluents.

As used herein, "pharmaceutically acceptable" (or "biologically acceptable") refers to materials characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

The term "pharmaceutically acceptable carriers, excipient, and/or diluents" refers to additives commonly used in the preparation of pharmaceutical compositions and includes, for example, solvents, dispersion media, saline solutions, surfactants, solubilizing agents, lubricants, emulsifiers, coatings, antibacterial and antifungal agents, chelating agents, pH-modifiers, soothing agents, buffers, reducing agents, antioxidants, isotonic agents, absorption delaying agents or the like. Such compositions may be prepared in a manner well known in the pharmaceutical art by mixing the antibody having a suitable degree of purity with one or more optional pharmaceutically acceptable carriers or excipients (see Remington: *The Science and Practice of Pharmacy*, by Loyd V Allen, Jr, 2012, $22^{nd}$ edition, Pharmaceutical Press; *Handbook of Pharmaceutical Excipients*, by Rowe et al., 2012, $7^{th}$ edition, Pharmaceutical Press). The carrier/excipient can be suitable for administration of the antibody by any conventional administration route, for example, for oral, intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration. In an embodiment, the carrier/excipient is adapted for administration of the antibody by the intravenous or subcutaneous route. In an embodiment, the carriers/excipients are adapted for administration of the antibody by the intravenous route. In another embodiment, the carriers/excipients are adapted for administration of the antibody thereof by the subcutaneous route.

The composition may also comprise one or more additional active agents for the treatment the targeted disease/condition or for the management of one or more symptoms of the targeted disease/condition (e.g., pain killers, anti-nausea agents, etc.), as described in more detail below.

The monovalent antibody of the present disclosure may be used to inhibit any biological, physiological and/or pathological process that involves GAL-7 activity, for example GAL-7 activity associated with homodimerization.

In another aspect, the present disclosure provides a method (in vitro or in vivo) for binding to GAL-7, said method comprising contacting said GAL-7 with the monovalent antibody or the composition described herein. In an embodiment, the above-mentioned method is for binding to GAL-7 in a cell or in the extracellular space (since prototypic galectins such as GAL-7 are released by cells via a non-classical secretory pathway). The present disclosure also provides the use of the monovalent antibody or the composition described herein for binding to GAL-7. The present disclosure also provides the use of the monovalent antibody or the composition described herein for the manufacture of a medicament for binding to GAL-7. The method or use for binding to GAL-7 may be useful in diagnostic, disease monitoring, prognostic or therapeutic application, notably to detect GAL-7, to identify and/or target GAL-7-expressing cells (e.g., by CAR cells), to deliver molecules (e.g., cytotoxic agents) to GAL-7-expressing cells.

In another aspect, the present disclosure provides a method (in vitro or in vivo) for inhibiting the dimerization of GAL-7, said method comprising contacting said GAL-7 with the monovalent antibody or the composition described herein. In an embodiment, the above-mentioned method is for inhibiting the dimerization of GAL-7 in a cell or in the extracellular space (since prototypic galectins such as GAL-7 are released by cells via a non-classical secretory pathway). The present disclosure also provides the use of the monovalent antibody or the composition described herein for inhibiting the dimerization of GAL-7. The present disclosure also provides the use of the monovalent antibody or the composition described herein for the manufacture of a medicament for inhibiting the dimerization of GAL-7.

Recombinant hGAL-7 has been shown to kill certain types of cells, such as Jurkat T cells, monocytes and human peripheral T cells, suggesting that GAL-7 has immunosuppressive properties. In another aspect, the present disclosure provides a method for inhibiting GAL-7-mediated apoptosis in a cell, said method comprising contacting said cell with the monovalent antibody or the composition described herein. The present disclosure also provides the use of the monovalent antibody or the composition described herein for inhibiting GAL-7-mediated apoptosis in a cell. The present disclosure also provides the use of the monovalent antibody or the composition described herein for the manufacture of a medicament for inhibiting GAL-7-mediated apoptosis in a cell. In an embodiment, the above-mentioned cell is an immune cell, such as a T lymphocyte or a monocyte. In another aspect, the present disclosure provides a method for inhibiting GAL-7-mediated immunosuppression in a subject, said method comprising administering to said subject an effective amount of the monovalent antibody or the composition described herein. The present disclosure also provides the use of the monovalent antibody or the composition described herein for inhibiting GAL-7-mediated immunosuppression in a subject. The present disclosure also provides the use of the monovalent antibody or the composition described herein for the manufacture of a medicament for inhibiting GAL-7-mediated immunosuppression in a subject. In an embodiment, the subject suffers from a GAL-7-expressing cancer. In an embodiment, the monovalent antibody reduces or inhibits the binding of extracellular GAL-7 to glycoreceptors expressed by infiltrated immune cells.

In another aspect, the present disclosure provides a method for treating a GAL-7-expressing cancer (e.g., inhibiting tumor growth and/or metastasis) in a subject, said method comprising administering to said subject an effective amount of the monovalent antibody or the composition described herein. The present disclosure also provides the use of the monovalent antibody or the composition described herein for treating a GAL-7-expressing cancer in a subject. The present disclosure also provides the use of the monovalent antibody or the composition described herein for the manufacture of a medicament for treating a GAL-7-expressing cancer in a subject.

In another aspect, the present disclosure provides a method for detecting, diagnosing and/or monitoring the progression of a GAL-7-expressing cancer (e.g., monitoring tumor size and/or metastasis) in a subject, said method comprising administering to said subject an effective amount of the monovalent antibody or the composition described herein. The present disclosure also provides the use of the monovalent antibody or the composition described herein for detecting, diagnosing and/or monitoring the progression of a GAL-7-expressing cancer in a subject. The present disclosure also provides the use of the monovalent antibody or the composition described herein for the manufacture of an agent for detecting, diagnosing and/or monitoring the progression of a GAL-7-expressing cancer in a subject.

GAL-7-expressing or GAL-7-overexpressing cancers include various carcinomas such as breast cancer (including triple-negative breast cancer), head and neck squamous cell carcinoma, cervical adeno-carcinoma, bladder squamous cell carcinoma, ovarian cancer and thyroid cancer, lymphomas and melanomas. In an embodiment, the monovalent antibody reduces or inhibits the binding of GAL-7 to glycosylated residues on cell surface receptors of tumor cells.

In an embodiment, the GAL-7-expressing cancer is of epithelial origin. In another embodiment, the GAL-7-expressing cancer is a breast cancer, a melanoma, an ovarian cancer or a lymphoma. In a further embodiment, the GAL-7-expressing cancer is a breast cancer. In another embodiment, the GAL-7-expressing cancer is an ovarian cancer. In another embodiment, the GAL-7-expressing cancer is a lymphoma. In another embodiment, the cancer is a cancer of neural cells, for example a medulloblastoma.

In another embodiment, the monovalent antibody could be used to treat other diseases or conditions in which GAL-7 activity may play a role in the etiology of the disease/condition, for example infectious diseases or diseases/injury of the skin, where GAL-7 is normally expressed (Gendronneau et al., *Mol Biol Cell*. 2008 December; 19(12):5541-9; Gendronneau et al., *PLoS One*. 2015 Mar. 5; 10(3): e0119031), in graft rejection (Luo et al., *Transplant Proc.* 2013 March; 45(2):630-4), asthma (Yin et al., *Zhonghua Er Ke Za Zhi*. 2006 July; 44(7):523-6), in preeclampsia and miscarriage (Menkhorst et al., *Placenta*. 2014 April; 35(4): 281-5 and *Placenta*. 2014 March; 35(3): 195-201), as well as eye diseases or conditions associated with pathological neovascularization/angiogenesis (ocular neovascularization), such as trachoma, corneal ulcers, keratoconjunctivitis (e.g., phlyctenular keratoconjunctivitis), keratitis (e.g., rosacea keratitis, interstitial keratitis, sclerosing keratitis), burns (e.g., chemical burns), ocular histoplasmosis, pathologic myopia, proliferative diabetic retinopathy, age-related macular degeneration (AMD), and retinopathy of prematurity (Cao et al., 2003, supra).

The amount of the monovalent antibody which is effective for the above-noted activities/therapeutic uses will depend on several factors including the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present disclosure should be sufficient to effect/induce a beneficial prophylactic and/or therapeutic response in the patient over time (in the case of a cancer, a decrease in tumor size, inhibition of tumor cell proliferation, increased survival time, etc.). The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In an embodiment, the above-mentioned treatment comprises the use/administration of more than one (i.e. a combination of) active/therapeutic agent, including the above-mentioned monovalent antibody. The combination of prophylactic/therapeutic agents and/or compositions of the present disclosure may be administered or co-administered (e.g., consecutively, simultaneously, at different times) in any conventional dosage form. Co-administration in the context of the present disclosure refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) or treatment currently used to prevent or treat the disorder in question (e.g., agents or treatments currently used in the treatment of cancers, such as radiotherapy, surgery and/or targeted therapy).

In an embodiment, the monovalent antibody described herein is used in combination with one or more chemotherapeutic agents. Examples of chemotherapeutic agents suitable for use in combination with the monovalent antibody described herein include, but are not limited to, *vinca* alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, platinum-based agents, anthracycline antibiotics, topoisomerase inhibitors, macrolides, retinoids (such as all-trans retinoic acids or a derivatives thereof), geldanamycin or a derivative thereof (such as 17-AAG), immunotherapeutic agents (e.g., immune checkpoint inhibitors such as PD-1/PD-L1 inhibitors and CTLA-4 inhibitors, B7-1/B7-2 inhibitors, CAR T cells) and other cancer therapeutic agents recognized in the art. In some embodiments, chemotherapeutic agents for use in combination with the monovalent antibody described herein comprise one or more of adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., taxol, paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, erlotinib, erbitux, PD-1/PD-L1 inhibitors (e.g., nivolumab, pembrolizumab, atezolizumab), CTLA-4 inhibitors (e.g., Ipilimumab), and derivatives thereof, and the like. In an embodiment, the monovalent antibody or composition comprising same described herein is used in combination with an EGFR or tyrosine kinase targeting agent, for example an EGFR inhibitor (RTK inhibitor). The monovalent antibody or composition comprising same described herein may also be used in combination with one or more additional therapeutic antibodies or antibody fragments, e.g., therapeutic antibodies or antibody fragments used for the treatment of tumors.

As used herein, the term "subject" is taken to mean warm blooded animals such as mammals, for example, cats, dogs, mice, guinea pigs, horses, bovine cows, sheep and humans. In an embodiment, the subject is a mammal, and more particularly a human.

MODE(S) FOR CARRYING OUT THE INVENTION

The present invention is illustrated in further details by the following non-limiting examples.

Example 1: Materials and Methods

Production of recombinant GAL-7. Codon-optimized cDNA encoding human GAL-7 was synthesized and subcloned into the pET-22b(+) vector for production in *E. coli* BL21 (DE3) cells as previously described [Vladoiu et al., 2015]. Purification was carried out using standard lactose affinity chromatography. Each preparation was dialyzed against phosphate buffered saline (PBS) to remove residual lactose. The functional integrity of each preparation was performed using the standard in vitro human Jurkat T cell model system, as previously described [Vladoiu et al., 2015].

Generation of Nbs. hGAL-7-specific Hybribody $V_H$Hs (Nanobodies, Nbs) were obtained following in vitro screening of a non-immune recombinant antibody synthetic library. For this, a library containing more than $3 \times 10^9$ humanized synthetic single domain antibody (hsd2Ab) clones expressed at the surface of M13 phage (Hybrigenics Services, Moutel et al., eLife 2016; 5:e16228) was screened, allowing selection of Nbs in the nM range. The library was subjected to three rounds of panning against immobilized recombinant human native GAL-7 devoid of carbohydrates in its GBS. All Nb sequences of the Nbs were inserted into the prokaryotic vector pHEN2 (with 6×His and cMyc Tags) for production in *E. coli* BL21 (DE3). The Nbs were purified by conventional immobilized metal ion affinity chromatography.

Biochemical analysis: Following their purification and lyophilization, each nanobody was biochemically evaluated for their propensity to disrupt the homodimeric conformation of GAL-7. This was tested in vitro using standard low SDS-PAGE and gel filtration methods, as previously described [Vladoiu et al., 2015].

Functional analysis: This was performed using the standard in vitro human Jurkat T cell model system. In brief, GAL-7 was incubated with or without increasing concentrations of Nbs before addition to Jurkat T cells. After 4 hours of incubation, apoptosis was measured by standard Western blot analysis using an anti-PARP-1 antibody. Additional experiments were carried out using annexin V/propidium iodide staining measured by flow cytometry, as previously described [Vladoiu et al., 2015].

Enzyme-linked immunosorbent assay (ELISA). ELISA was performed to analyze cross-reactivity of GAL-7-Nbs with mouse GAL-7. Wells of microtiter plate (NUNC, MaxiSorp, ThermoFisher) were coated with 100 µl (5 µM) of human recombinant GAL-7 or mouse recombinant GAL-7 (Abcam) in 0.1 M carbonate buffer pH 9.5 overnight at 4° C. Plates were emptied, rinsed three times with PBS and blocked with 100 µl of PBA (PBS containing 1% (v/v) bovine serum albumin) for 1 h at room temperature. After washing with PBS, Nbs were diluted in PBA at the indicated concentrations and a volume of 100 µl of each concentration was added to each well. Following a 1 h incubation at room temperature, plates were emptied and rinsed three times with PBS. A goat anti-His-Tag conjugate (1:1000, Bio-Rad) was added to each well followed by a 1 h incubation at room temperature. After rinsing and washing with PBS, plates were probed for 1 h at room temperature with 100 µl of an anti-goat IgG-horseradish peroxidase (HRP) conjugate (1:1000, R&D Systems). After washing, bound HRP conjugate was detected using 3,30,5,50-tetramethylbenzidine (1:1000, TMB, Sigma) as substrate. The end product was measured at 450 nm. For each sample, experimental and control reactions were run in triplicate.

SPR analysis. Binding affinities of his-tagged GAL-7-specific Nbs was measured by surface plasmon resonance (SPR) using a BIACore® system. Briefly, a buffer flow was run across the sensor surface, which has previously been coated with human GAL-7, then the Nbs were introduced into the device and allowed to bind to the immobilized antigen. The stability of the binding between GAL-7 and the Nbs was measured and used to calculate the dissociation constant (Kd) of the Nbs for human GAL-7.

Determination of aliphatic index of Nbs. The aliphatic index represents the relative volume occupied by side chains of aliphatic residues (alanine, valine, isoleucine, leucine) in a given amino acid protein sequence. It was estimated according to the method described in Ikai, A. 1980 Thermostability and aliphatic index of globular proteins. J Biochem. 88(6): 1895-1898.

Determination of instability index of Nbs. To establish an instability index, a statistical analysis was performed on known stable (32) and unstable (12) proteins. From the amino acid composition study of these proteins, a weight value of instability was assigned to each dipeptide which are now used to predict stability characteristics of a protein (Guruprasad, K. et al. 1990. Correlation between stability of a protein and its dipeptide composition: a novel approach for prediction in vivo stability of a protein from its primary sequence. Protein Eng. 4(2): 155-161).

Determination of half-life of Nbs. Half-life of a protein represents the predicted time to degrade a protein following the N-end rule which is based on ubiquitination pathways in accordance with N-terminal residues recognized by ubiquitin ligases in prokaryotic or eukaryotic organisms (Bachmair, A. et al. 1986. In vivo half-life of a protein is a function of its amino-terminal residue. *Science.* 234(4773): 179-186).

Example 2: Generation of GAL-7-Specific Nbs

Figure 3A:
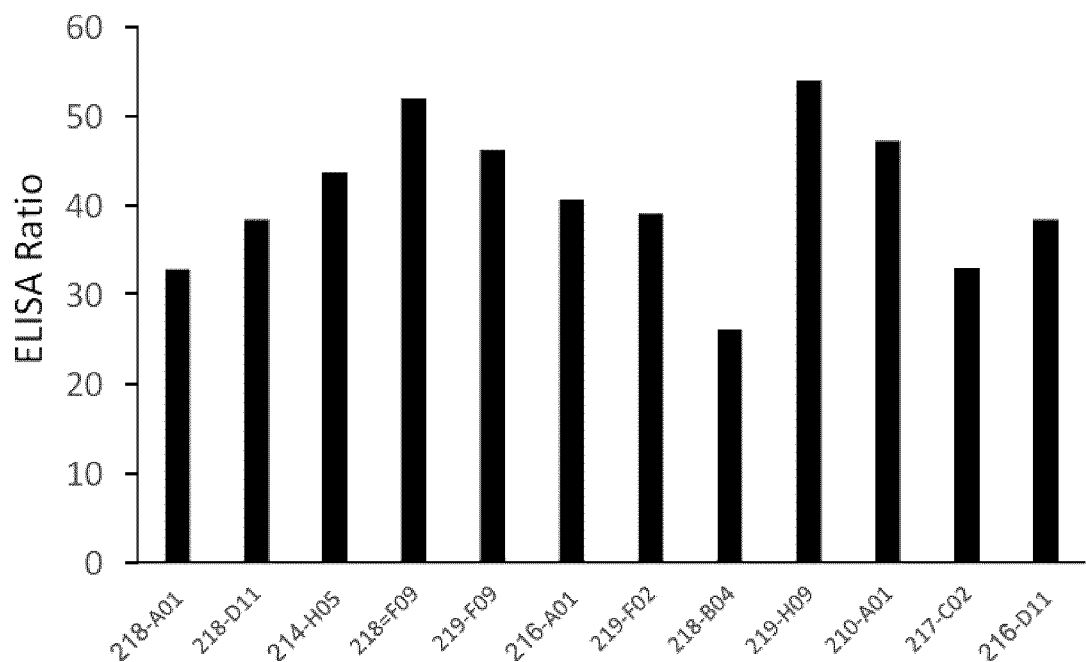

A synthetic library of humanized synthetic llama single domain antibody (hs2dAb) was used to generate high affinity Nbs without animal immunization [Moutel et al., 2016]. This technology was used to generate 12 different Nbs that specifically bind hGAL-7 (FIG. 3A). As shown in the amino acid sequences depicted in FIG. 3B, more than half of the Nbs have a CDR3 harboring 12-18 residues, a favorable feature to target hidden or buried epitopes.

Example 3: Characterization of GAL-7-Specific Nbs

Some physicochemical characteristics of the 12 Nbs whose sequences are depicted in FIG. 3 were determined and are presented in Table I.

Representative Nbs among the "hits" were further characterized, notably for their ability to inhibit GAL-7-induced killing of human activated T cells or to inhibit GAL-7 homodimerization (Table II).

TABLE II

Effect of representative GAL7-specific Nbs on GAL -7 dimers and GAL-7-induced killing of human activated T cells

| Nabs | Dimer inhibition | Inhibitory activity* |
|---|---|---|
| 214_H05 | Not tested | No |
| 216_A01 | Yes | Yes |
| 218_A01 | Not tested | No |
| 218_B04 | Not tested | No |
| 218_D11 | No | No |
| 218_F09 | No | No |
| 219_A01 | No | No |
| 219_F02 | Not tested | Yes |
| 219_F09 | Not Tested | No |
| 219_H09 | Not tested | Yes |
| 216_D11 | Not tested | No |
| 217_C02 | Yes | Yes |

*Inhibition of GAL-7-induced killing of human activated T cells

Figure 4:
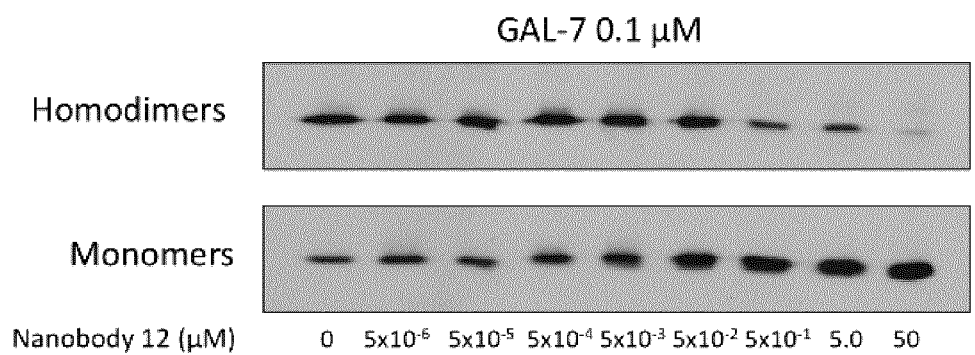
FIG. 4 depicts a Western blot showing the disruption of human GAL-7 (hGAL-7) dimer by a representative nanobody (NB #12, corresponding to 217_C02 in FIG. 3B). Recombinant hGAL-7 was incubated with increasing concentrations of NB #12. The effect of NB #12 on the monomeric and dimeric hGAL-7 forms was assessed by Western blotting in semi-native PAGE gels with GAL-7-specific polyclonal antibodies.
Figure 4:
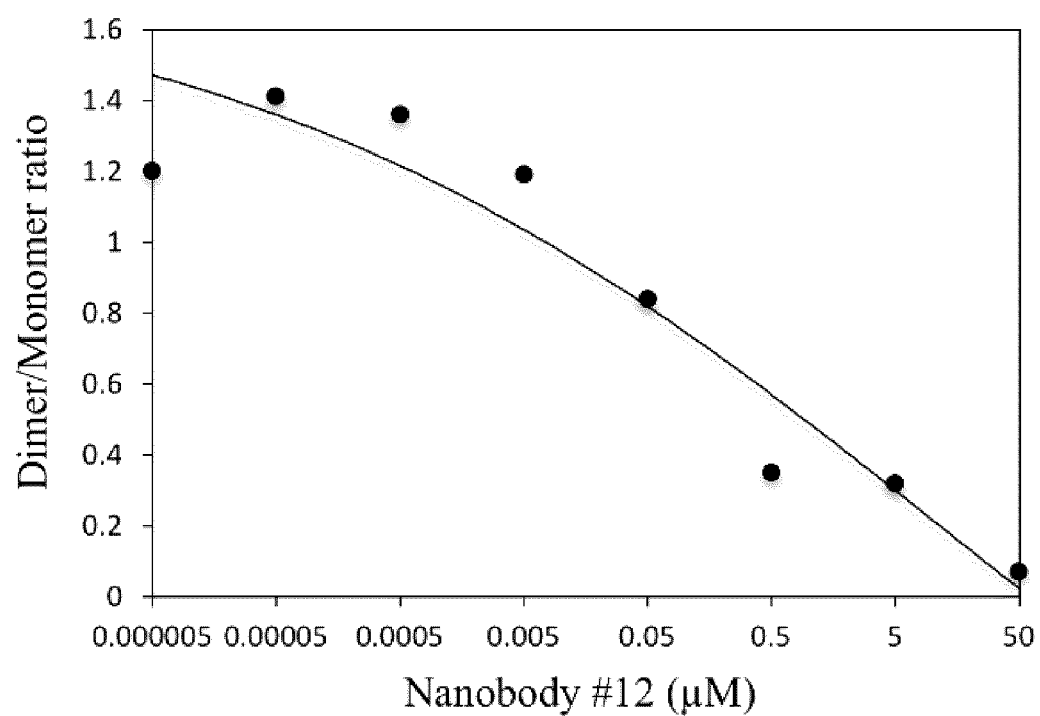
Figure 5:
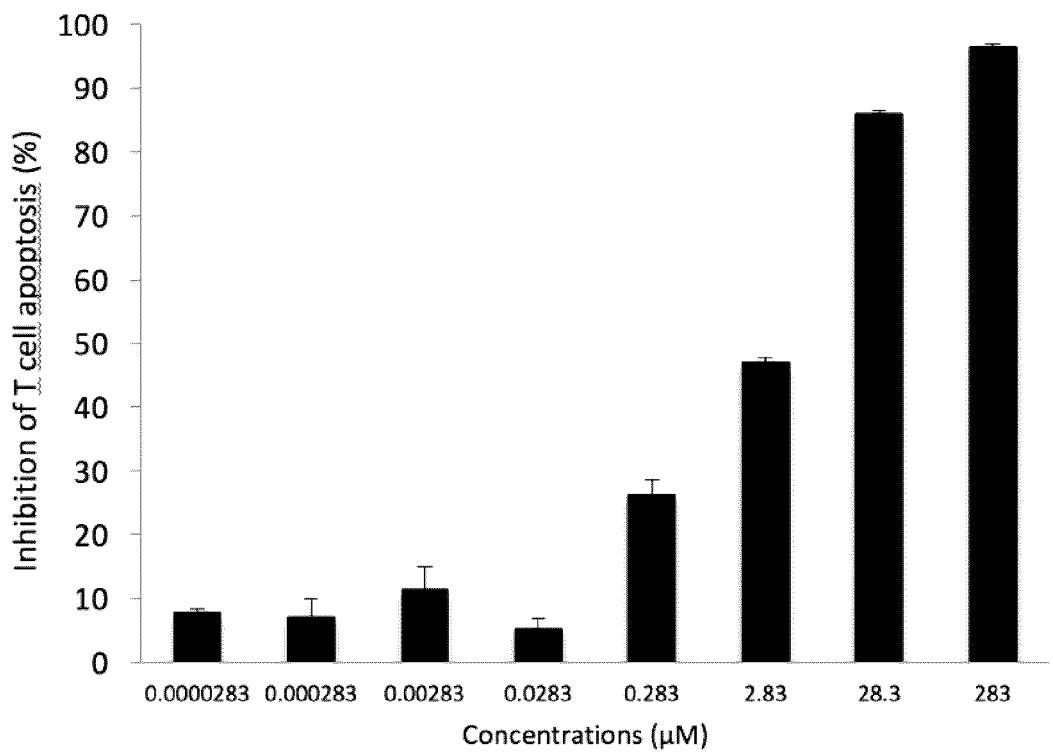
FIG. 5 shows the inhibition of GAL-7-induced apoptosis of human T cells by a representative nanobody (NB #2, corresponding to 216_A01 in FIG. 3B). Jurkat T cells were incubated with recombinant hGAL-7 in the presence of increasing concentrations of NB #2. Apoptosis was measured by standard Annexin V staining by flow cytometry.
Figure 6:
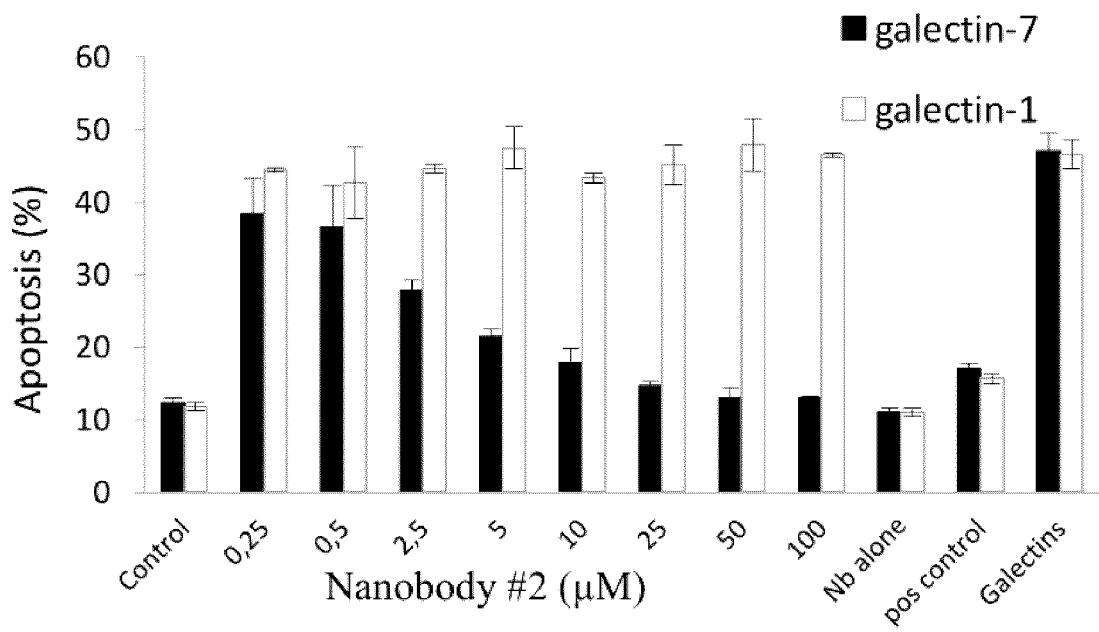
FIG. 6 shows the inhibition of GAL-7-induced apoptosis of human T cells by a representative nanobody (NB #2, corresponding to 216_A01 in FIG. 3B). Jurkat T cells were incubated with recombinant hGAL-7 or hGAL-1 in the presence of increasing concentrations of NB #2. Controls included Jurkat T cells without recombinant galectins (Control), Jurkat T cells incubated with NB #2 only (Nb alone), GAL-7 or GAL-1 alone (Galectins) and a positive control for inhibition (pos, incubation with N-Acetyl-D-lactosamine, LacNAc). Apoptosis was measured by standard Annexin V staining by flow cytometry.

Several potential "leads" capable of disrupting GAL-7 homodimers (notably 216_A01 and 217_C02) and/or inhibiting GAL-7-induced killing of human activated T cells (including 217_C02, 218_F09, 216_D11 and 216_A01) were identified. The results shown in FIG. 4, Nb 217_C02 (SEQ ID NO:52) is very efficient in its ability to prevent the formation of GAL-7 homodimers. 216_A01 was very effective in inhibiting GAL-7-induced killing of human activated T cells (FIG. 5). As evidenced by the results depicted in FIG.

TABLE I

Physicochemical characteristics of representative GAL7-specific Nbs

| Nabs | a.a.* | MW | pI | Half-life** | Inst. Index | Ali. Index*** |
|---|---|---|---|---|---|---|
| 214_H05 | 181 | 19672.52 | 5.71 | 30 h | 34.84 | 65.36 |
| 216_A01 | 175 | 19273.06 | 5.31 | 30 h | 45.11 | 63.71 |
| 218_A01 | 175 | 18629.40 | 5.29 | 30 h | 36.49 | 64.29 |
| 218_B04 | 175 | 18940.69 | 5.07 | 30 h | 38.28 | 65.37 |
| 218_D11 | 178 | 19632.54 | 5.45 | 30 h | 42.59 | 62.08 |
| 218_F09 | 178 | 1900.71 | 5.16 | 30 h | 37.54 | 63.20 |
| 219_A01 | 169 | 18190.74 | 5.03 | 30 h | 36.96 | 62.54 |
| 219_F02 | 184 | 20058.02 | 5.05 | 30 h | 34.57 | 63.26 |
| 219_F09 | 175 | 18695.36 | 4.85 | 30 h | 36.36 | 65.43 |
| 219_H09 | 184 | 20067.05 | 5.61 | 30 h | 31.64 | 66.96 |
| 216_D11 | 181 | 19627.44 | 5.05 | 30 h | 39.79 | 61.10 |
| 217_C02 | 181 | 19639.46 | 5.09 | 30 h | 36.17 | 63.76 | a.a. = number of amino acids;
MW = Molecular weight;
pI = isoelectric point;
Inst. Index = Instability index;
Ali. Index = Aliphatic index;
*In addition to the sequences depicted in FIG. 3B, the Nbs tested include at the C-terminal end: a 3-alanine linker, a His tag and 3 c-myc tags (sequence: AAAHHHHHHGAAEQKLISEEDLNGAAEQKLISEEDLN-GAAEQKLISEEDLNGAA (SEQ ID NO: 54) to facilitate purification.
**in mammalian reticulocytes in vitro;
***higher Aliphatic Index usually reflects increased thermostability All of the Nabs have a predicted half-life of 30 h, and most of the Nabs have an instability Index below 40, which usually predicts a stable protein in vitro. Thus, based on these physicochemical properties, these Nabs may be expected to be suitable for use as diagnostic and/or therapeutic agents.

6 for 216_A01, the anti-GAL-7 Nbs described herein do not appear to have detectable inhibitory activity against other human galectins (hGAL-1), indicating GAL-7 specificity. Surface plasmon resonance (SPR) binding analysis showed that two representative Nbs have a high affinity for GAL-7 (Nb 216_A01 (SEQ ID NO: 6): $K_d$=0.122 µm, Nb 217_C02

(SEQ ID NO:52): $K_d$=1.495 µm) (Table III). The most promising "hits" also show strong cross-reactivity with mouse GAL-7, which shares high sequence homology with human GAL-7 (106 out of 136 identical residues).

TABLE III

Results of surface plasmon resonance (SPR) analysis of two representative nanobodies (NB 216_A01 and 217_C02)

| Analyte | Channel | $k_a$ (M$^{-1}$s$^{-1}$) | $k_d$ (s$^{-1}$) | $K_D$ (µM) | $R_{max}$ (RU) | Chi$^2$ (RU$^2$) |
|---|---|---|---|---|---|---|
| Nanobody 216_A01 (SEQ ID NO: 6) | Fc = All − 01 | 28370 ± 250 | 0.003479 ± 1.8E−5 | 0.1226 | 21.2 ± 0.031<br>25.4 ± 0.039<br>36.3 ± 0.065 | 0.301 |
| Nanobody 217_C02 (SEQ ID NO: 52) | Fc = 2 − 1 | 1105 ± 8.1 | 0.001651 ± 6.8E−6 | 1.495 | 14.5 ± 0.064 | 0.413 |

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Barondes S H, Cooper D N, Gitt M A, Leffler H. (1994). Galectins. Structure and function of a large family of animal lectins. *J Biol Chem* 269, 20807-10.
2. Blanchetot C, Verzijl D, Mujić-Delić A, Bosch L, Rem L, et al. 2013. Neutralizing nanobodies targeting diverse chemokines effectively inhibit chemokine function. *J Biol Chem* 288, 25173.
3. Daley D, Mani V R, Mohan N, Akkad N, Ochi A, et al. 2017. Dectin 1 activation on macrophages by galectin 9 promotes pancreatic carcinoma and peritumoral immune tolerance. *Nat Med* 23, 556.
4. De Genst E, Silence K, Decanniere K, Conrath K, Loris R, Kinne J, Muyldermans S, Wyns L. 2006. Molecular basis for the preferential cleft recognition by dromedary heavy-chain antibodies. *Proc Nat Acad Sci* 103, 4586.
5. Gauthier L, Rossi B, Roux F, Termine E, Schiff C. 2002. Galectin-1 is a stromal cell ligand of the pre-B cell receptor (BCR) implicated in synapse formation between pre-B and stromal cells and in pre-BCR triggering. *Proc Natl Acad Sci* 99, 13014.
6. Hamers-Casterman C, Atarhouch T, Muyldermans S, Robinson G, Hamers C, Songa E B, Bendahman N, Hamers R. 1993. Naturally occurring antibodies devoid of light chains. *Nature* 363, 446.
7. Kamitori S. 2018. Three-Dimensional Structures of Galectins. *Trends Glycosci. Glycotechnol.* 2018 30(172): SE41-SE50.
8. Komath S S, Kavitha M, Swamy M J. Beyond carbohydrate binding: new directions in plant lectin research. *Org Biomol Chem*. 2006 Mar. 21; 4(6):973-88.
9. Leonidas D D, Vatzaki E H, Vorum H, Celis J E, Madsen P, Acharya K R. 1998. Structural basis for the recognition of carbohydrates by human galectin-7. *Biochemistry* 37, 13930.
10. Levi G, Tarrab-Hazdai R, Teichberg V I. 1983. Prevention and therapy with electrolectin of experimental autoimmune myasthenia gravis in rabbits. *Eur J Immunol* 13, 500.
11. Liu F T, Rabinovich G A. 2005. Galectins as modulators of tumour progression. *Nat Rev Cancer* 5, 29.
12. Lykken J M, Horikawa M, Minard-Colin V, Kamata M, Miyagaki T, Poe J C, Tedder T F. 2016. Galectin-1 drives lymphoma CD20 immunotherapy resistance: validation of a preclinical system to identify resistance mechanisms. *Blood* 127, 1886.
13. Morris S., Ahmad N., André S., Kaltner H., Gabius H. J., Brenowitz M, Brewer F. 2004. Quaternary solution structures of galectins-1, -3, and -7. *Glycobiology* 14, 293.
14. Moutel S, Bery N, Bernard V, Keller L, Lemesre E, et al. 2016. NaLi-H1: A universal synthetic library of humanized nanobodies providing highly functional antibodies and intrabodies. *Elife* 5.
15. Nabi I R, Shankar J, Dennis J W. 2015. The galectin lattice at a glance. *J Cell Sci* 128, 2213.
16. Offner H, Celnik B, Bringman T S, Casentini-Borocz D, Nedwin G E, Vandenbark A A. 1990. Recombinant human β-galactoside binding lectin suppresses clinical and histological signs of experimental autoimmune encephalomyelitis. *J Neuroimmunol* 28, 177.
17. Perillo N L, Pace K E, Seilhamer J J, Baum L G. (1995). Apoptosis mediated of T cells mediated by galectin-1. *Nature* 378, 736-9.
18. Rodriguez E, Schetters S T, van Kooyk Y. 2018. The tumour glyco-code as a novel immune checkpoint for immunotherapy. *Nat Rev Immunol* 18, 204.
19. Salatino M, Dalotto-Moreno T, Rabinovich G A. 2013. Thwarting galectin-induced immunosuppression in breast cancer. *Oncoimmunology* 2, e24077.
20. Than N G, Balogh A, Romero R, Kárpáti É, Erez O, et al. 2014. Placental protein 13 (PP13) — a placental immunoregulatory galectin protecting pregnancy. *Front Immunol* 5, 348.
21. Van Woensel M, Mathivet T, Wauthoz N, Rosière R, Garg A D, et al. 2017. Sensitization of glioblastoma tumor micro-environment to chemo- and immunotherapy by Galectin-1 intranasal knock-down strategy. *Sci Rep* 7, 1217.
22. Vladoiu M C, Labrie M, Létourneau M, Egesborg P, Gagné D, Billard É, Grosset A A, Doucet N, Chatenet D, St-Pierre Y. 2015. Design of a peptidic inhibitor that targets the dimer interface of a prototypic galectin. *Oncotarget* 6, 40970.
23. Yildirim C, Vogel D Y, Hollander M R, Baggen J M, Fontijn R D, Nieuwenhuis S, Haverkamp A, de Vries M R, Quax P H, Garcia-Vallejo J J, van der Laan A M, Dijkstra C D, van der Pouw Kraan T C, van Royen N, Horrevoets A J. 2015. Galectin-2 induces a proinflammatory, anti-arteriogenic phenotype in monocytes and macrophages. *PLoS One* e0124347.

What is claimed is:

1. A monovalent antibody that specifically binds to human galectin-7 (hGAL-7), wherein the monovalent antibody comprises one of the following combinations of complementary determining regions (CDRs):
   (a) a CDR1 comprising the sequence AGSRSDV (SEQ ID NO:12); a CDR2 comprising the sequence GFWGWTT (SEQ ID NO:13); and a CDR3 comprising the sequence LGGAPGQTG (SEQ ID NO:14);
   (b) a CDR1 comprising the sequence DTSRFDV (SEQ ID NO:15); a CDR2 comprising the sequence WWSSDHI (SEQ ID NO:16); and a CDR3 comprising the sequence YGEYPPRMNRRP (SEQ ID NO:17);
   (c) a CDR1 comprising the sequence TTSNSSG (SEQ ID NO:18); a CDR2 comprising the sequence WDHGILT (SEQ ID NO:19); and a CDR3 comprising the sequence HGYVHFNMTHRHISD (SEQ ID NO:20);
   (d) a CDR1 comprising the sequence TTSNGEV (SEQ ID NO:21); a CDR2 comprising the sequence FGAGSSE (SEQ ID NO:22); and a CDR3 comprising the sequence ASWYHSSIGSMS (SEQ ID NO:23);
   (e) a CDR1 comprising the sequence AYSFESG (SEQ ID NO:24); a CDR2 comprising the sequence SDADLFS (SEQ ID NO:25); and a CDR3 comprising the sequence AFSSGGELS (SEQ ID NO: 26);
   (f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29);
   (g) a CDR1 comprising the sequence STSYSST (SEQ ID NO:30); a CDR2 comprising the sequence FDGTSKP (SEQ ID NO:31); and a CDR3 comprising the sequence AGEWEALMWPPVHDFWIY (SEQ ID NO:32);
   (h) a CDR1 comprising the sequence RTSSQDI (SEQ ID NO:33); a CDR2 comprising the sequence DYSGGNV (SEQ ID NO:34); and a CDR3 comprising the sequence FLGEEKTSW (SEQ ID NO:35);
   (i) a CDR1 comprising the sequence STSYGET (SEQ ID NO:36); a CDR2 comprising the sequence YYSTRKP (SEQ ID NO:37); and a CDR3 comprising the sequence IVAYIYADGVRGYHQKID (SEQ ID NO:38);
   (j) a CDR1 comprising the sequence GGYDWDA (SEQ ID NO:39); a CDR2 comprising the sequence SNNNGSR (SEQ ID NO:40); and a CDR3 comprising the sequence ADQ;
   (k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44); or
   (l) a CDR1 comprising the sequence DTSESTS (SEQ ID NO:45); a CDR2 comprising the sequence RSSTWDA (SEQ ID NO:46); and a CDR3 comprising the sequence MADIFDHPQNASFMK (SEQ ID NO:47).

2. The monovalent antibody of claim 1, wherein the monovalent antibody inhibits hGAL-7 activity and comprises one of the following combinations of CDRs:
   (f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29);
   (g) a CDR1 comprising the sequence STSYSST (SEQ ID NO:30); a CDR2 comprising the sequence FDGTSKP (SEQ ID NO:31); and a CDR3 comprising the sequence AGEWEALMWPPVHDFWIY (SEQ ID NO:32);
   (i) a CDR1 comprising the sequence STSYGET (SEQ ID NO:36); a CDR2 comprising the sequence YYSTRKP (SEQ ID NO:37); and a CDR3 comprising the sequence IVAYIYADGVRGYHQKID (SEQ ID NO:38); or
   (k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44).

3. A method for inhibiting galectin-7-mediated apoptosis in a cell, said method comprising contacting said cell with an effective amount of the monovalent antibody of claim 2.

4. A method for treating an eye disease or condition associated with pathological neovascularization or angiogenesis in a subject, said method comprising administering to said subject an effective amount of the monovalent antibody of claim 2.

5. The method of claim 4, wherein the eye disease or condition is trachoma, corneal ulcer, keratoconjunctivitis, keratitis, chemical burn, ocular histoplasmosis, pathologic myopia, proliferative diabetic retinopathy, age-related macular degeneration, or retinopathy of prematurity.

6. The monovalent antibody of claim 1, wherein the monovalent antibody inhibits hGAL-7 dimerization and comprises one of the following combinations of CDRs:
   (f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29); or
   (k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44).

7. The monovalent antibody of claim 6, wherein the monovalent antibody comprises the following combination of CDRs:
   (f) a CDR1 comprising the sequence RYSRIEI (SEQ ID NO:27); a CDR2 comprising the sequence STPSSNE (SEQ ID NO:28); and a CDR3 comprising the sequence RWDWHSWDT (SEQ ID NO:29).

8. The monovalent antibody of claim 6, wherein the nonvalent antibody comprises the following combination of CDRs:
   (k) a CDR1 comprising the sequence TYSSIEV (SEQ ID NO:42); a CDR2 comprising the sequence FEPNEFA (SEQ ID NO:43); and a CDR3 comprising the sequence SSVEWRQNGKPNTAS (SEQ ID NO:44).

9. A method for inhibiting the dimerization of human galectin-7 comprising contacting said galectin-6 with the monovalent antibody of claim 5.

10. The monovalent antibody of claim 1, wherein the monovalent antibody is a single-domain antibody.

11. The monovalent antibody of claim 1, which comprises:
   (i) a framework region (FR) 1 comprising an amino acid sequence having at least 50% identity with the sequence MAEVQLQASGGGFVQPGGSLRLS-CAASG (SEQ ID NO: 48);
   (ii) a FR2 comprising an amino acid sequence having at least 50% identity with the sequence MGWFRQAPGKEREFVSAIS (SEQ ID NO:49);
   (iii) a FR3 comprising or consisting of an amino acid sequence having at least 50% identity with the sequence; YYADSVKGRFTIS-RDNSKNTVYLQMNSLRAEDTATYYCA (SEQ ID NO:50);

(iv) a FR4 comprising an amino acid sequence having at least 50% identity with the sequence YWGQGTQVTVSS (SEQ ID NO:51); or (v) any combination of (i) to (iv).

12. The monovalent antibody of claim 11, which comprises:

(i) a FR1 comprising the sequence MAEVQLQASGGGFVQPGGSLRLSCAASG (SEQ ID NO: 48);

(ii) a FR2 comprising the sequence MGWFRQAPGKEREFVSAIS (SEQ ID NO:49);

(iii) a FR3 comprising the sequence YYADSVKGRFTIS-RDNSKNTVYLQMNSLRAEDTATYYCA (SEQ ID NO:50);

(iv) a FR4 comprising the sequence YWGQGTQVTVSS (SEQ ID NO:51); or (v) any combination of (i) to (iv).

13. The monovalent antibody of claim 1, comprising an amino acid sequence set forth in any one of SEQ ID NOs: 1-10, 52 and 53.

14. The monovalent antibody of claim 1, comprising an amino acid sequence set forth in any one of SEQ ID NOs: 6, 7, 9 and 52.

15. The monovalent antibody of claim 1, comprising an amino acid sequence set forth in SEQ ID NO:6 or 52.

16. The monovalent antibody of claim 1, wherein said antibody is conjugated to a label, a nanoparticle, a drug, a peptide, a nucleic acid, a toxin, an enzyme, a radioisotope, or a half-life extending moiety.

17. A pharmaceutical composition comprising the monovalent antibody defined in claim 1 and one or more pharmaceutically acceptable carriers, excipient, and/or diluents.

18. A method for binding human galectin-7 (hGAL-7) comprising contacting said hGAL-7 with the monovalent antibody of claim 1.

19. A method for treating a galectin-7-expressing cancer in a subject, said method comprising administering to said subject an effective amount of the monovalent antibody of claim 1.

20. The method of claim 19, wherein the cancer is a breast cancer, a melanoma, an ovarian cancer or a lymphoma.

* * * * *

UNITED STATES PATENT AND TRADEMARK OFFICE
CERTIFICATE OF CORRECTION

PATENT NO. : 12,195,541 B2
APPLICATION NO. : 17/421476
DATED : January 14, 2025
INVENTOR(S) : Chatenet et al.

Page 1 of 1

It is certified that error appears in the above-identified patent and that said Letters Patent is hereby corrected as shown below:

In the Specification

Column 4, Line 16: Please insert a paragraph break between "NO:29);" and "(g)"

In the Claims

Column 62, Line 53, Claim 9: Please correct "galectin-6" to read --galectin-7--

Signed and Sealed this
Eighth Day of July, 2025

Coke Morgan Stewart
*Acting Director of the United States Patent and Trademark Office*